US012751611B2

(12) United States Patent
Bi et al.

(10) Patent No.: US 12,751,611 B2
(45) Date of Patent: Oct. 6, 2026

(54) MOTOR CONTROL FOR DISPOSABLE STEERABLE ENDOSCOPE

(71) Applicant: Covidien LP, Mansfield, MA (US)

(72) Inventors: Chenghao Bi, Boulder, CO (US); Evan William Tuer, Cupar (GB); Derek S. Tata, Longmont, CO (US)

(73) Assignee: Covidien LP, Mansfield, MA (US)

( * ) Notice: Subject to any disclaimer, the term of this patent is extended or adjusted under 35 U.S.C. 154(b) by 178 days.

(21) Appl. No.: 18/421,476

(22) Filed: Jan. 24, 2024

(65) Prior Publication Data

US 2024/0252029 A1 Aug. 1, 2024

Related U.S. Application Data

(60) Provisional application No. 63/482,396, filed on Jan. 31, 2023.

(51) Int. Cl.
*A61B 1/267* (2006.01)
*A61B 1/00* (2006.01)
(Continued)

(52) U.S. Cl.
CPC ............ *A61B 1/267* (2013.01); *A61B 1/0004* (2022.02); *A61B 1/00052* (2013.01);
(Continued)

(58) Field of Classification Search
CPC ... A61B 1/267; A61B 1/0004; A61B 1/00052; A61B 1/0024; A61B 1/0057; A61B 17/0218; A61B 1/227; A61B 1/2671
(Continued)

(56) References Cited

U.S. PATENT DOCUMENTS 4,499,895 A * 2/1985 Takayama ............ A61B 1/0052 388/930
8,194,122 B2 6/2012 Amling et al.
(Continued)

FOREIGN PATENT DOCUMENTS

EP 2433553 A1 3/2012
JP 2014210085 A 11/2014
(Continued)

OTHER PUBLICATIONS

Ambu_aScope_3_Large_Brochure_4963605 (Oct. 2017).
(Continued)

*Primary Examiner* — Eduardo C Robert
*Assistant Examiner* — Tara Rose E Carter

(57) ABSTRACT

The technology relates to a medical video system that includes a video laryngoscope, a cartridge removably attached to the housing of the video laryngoscope, and an introducer such as endoscope. The cartridge may include a port, an output drive, and first electrical contacts. The endoscope may include a proximal end having a drive system and second electrical contacts. The proximal end of the endoscope is sized to enter the port, align the second electrical contacts with the first electrical contacts, and engage the drive system with the output drive such that movement of the output drive causes movement of the drive system. The video laryngoscope is programmed to receive a steering input on the display screen, translate the steering input into a movement of the drive output, and transmit a steering signal to cause the movement of the output drive.

20 Claims, 12 Drawing Sheets

(51) Int. Cl.
*A61B 1/005* (2006.01)
*A61B 1/05* (2006.01)

(52) U.S. Cl.
CPC ........ *A61B 1/00124* (2013.01); *A61B 1/0057* (2013.01); *A61B 1/05* (2013.01)

(58) Field of Classification Search
USPC .................................. 600/184–245, 141–149
See application file for complete search history.

(56) References Cited

U.S. PATENT DOCUMENTS

| | | | | |
|---|---|---|---|---|
| 8,652,033 | B2 | 2/2014 | Berci et al. | |
| 8,715,172 | B1 | 5/2014 | Girgis | |
| 8,746,239 | B2 | 6/2014 | Yoshida | |
| 8,827,899 | B2 | 9/2014 | Farr et al. | |
| 8,982,199 | B2 | 3/2015 | Amling et al. | |
| 9,123,155 | B2 | 9/2015 | Cunningham et al. | |
| 9,498,112 | B1 | 11/2016 | Stewart et al. | |
| 9,538,908 | B2 | 1/2017 | Allyn et al. | |
| 9,687,141 | B2 | 6/2017 | McGrath | |
| 9,820,641 | B2 | 11/2017 | McGrath | |
| 10,010,379 | B1 | 7/2018 | Gibby et al. | |
| 10,149,957 | B2 | 12/2018 | Runnels | |
| 2007/0197896 | A1 | 8/2007 | Moll et al. | |
| 2007/0236514 | A1 | 10/2007 | Agusanto et al. | |
| 2008/0177146 | A1 | 7/2008 | Chen | |
| 2008/0177148 | A1 | 7/2008 | Chen et al. | |
| 2008/0249355 | A1* | 10/2008 | Birnkrant | A61B 1/267 600/169 |
| 2008/0312507 | A1 | 12/2008 | Kim | |
| 2011/0130632 | A1 | 6/2011 | McGrail et al. | |
| 2011/0137127 | A1 | 6/2011 | Schwartz | |
| 2011/0245609 | A1* | 10/2011 | Laser | A61B 1/00052 600/109 |
| 2013/0057667 | A1 | 3/2013 | McGrath | |
| 2013/0267838 | A1 | 10/2013 | Fronk et al. | |
| 2014/0031700 | A1 | 1/2014 | Ferrantelli | |
| 2014/0160261 | A1 | 6/2014 | Miller et al. | |
| 2014/0275760 | A1 | 9/2014 | Lee et al. | |
| 2014/0378763 | A1 | 12/2014 | Atarot | |
| 2016/0199009 | A1 | 7/2016 | Gilboa | |
| 2016/0279365 | A1 | 9/2016 | Esnouf | |
| 2017/0055809 | A1 | 3/2017 | Omoto | |
| 2017/0209071 | A1 | 7/2017 | Zhao et al. | |
| 2017/0258313 | A1 | 9/2017 | McGrath | |
| 2018/0193102 | A1 | 7/2018 | Inoue | |
| 2018/0292199 | A1 | 10/2018 | Tojo et al. | |
| 2018/0296281 | A1 | 10/2018 | Yeung et al. | |
| 2018/0324352 | A1 | 11/2018 | Furuhata | |
| 2019/0133430 | A1 | 5/2019 | Inglis et al. | |
| 2019/0142262 | A1* | 5/2019 | Inglis | A61B 1/00048 600/188 |
| 2020/0029793 | A1 | 1/2020 | McGrath | |
| 2020/0195903 | A1 | 6/2020 | Komp et al. | |
| 2020/0254204 | A1 | 8/2020 | Moffat et al. | |
| 2020/0275824 | A1 | 9/2020 | Tata | |
| 2020/0367742 | A1 | 11/2020 | McGrath | |
| 2020/0383561 | A1 | 12/2020 | McGrath | |
| 2021/0052140 | A1* | 2/2021 | Tata | A61B 5/067 |
| 2021/0121155 | A1 | 4/2021 | Maguire | |
| 2021/0127949 | A1 | 5/2021 | Tata | |
| 2021/0128033 | A1 | 5/2021 | Tata | |
| 2021/0137350 | A1 | 5/2021 | Inglis | |
| 2021/0257856 | A1 | 8/2021 | Ng | |
| 2021/0259536 | A1 | 8/2021 | Inglis | |
| 2021/0275008 | A1 | 9/2021 | McGrath | |
| 2021/0318382 | A1 | 10/2021 | McGrath | |
| 2022/0110504 | A1 | 4/2022 | Inglis | |
| 2022/0225859 | A1 | 7/2022 | Phillips | |
| 2022/0257092 | A1 | 8/2022 | Ng | |
| 2022/0322942 | A1* | 10/2022 | Takahata | A61B 1/00096 |
| 2022/0354380 | A1 | 11/2022 | Tata | |
| 2023/0029630 | A1 | 2/2023 | Ng | |

FOREIGN PATENT DOCUMENTS

| | | |
|---|---|---|
| WO | 2020/005890 A1 | 1/2020 |
| WO | 2022/133248 | 6/2022 |
| WO | 2022/266500 | 12/2022 |

OTHER PUBLICATIONS

Mcgrath Mac—Video Laryngoscope Operator's Manual Instructions for Use—Aircraft Medical Ltd (2017) www.aircraftmedical.com—23 pages.

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx.doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," PLOS ONE | https://doi.org/10.1371/journal.pone.0186691 (Nov. 3, 2017).

* cited by examiner

MOTOR CONTROL FOR DISPOSABLE STEERABLE ENDOSCOPE

CROSS-REFERENCE TO RELATED APPLICATIONS

This application claims the benefit of U.S. Provisional Application No. 63/482,396 filed Jan. 31, 2023, entitled, "Motor Control for Disposable Steerable Endoscope," which is incorporated herein by reference in its entirety.

BACKGROUND

Laryngoscopes are commonly used to perform intubations on patients who require breathing assistance. During an intubation, the laryngoscope may be used to manipulate the anatomy of the larynx and structures associated with a patient's airway, in order to obtain a view sufficient for insertion of a breathing tube (e.g., an endotracheal tube) into the trachea. In some situations, the anatomy of the patient, or injury or other health condition of the patient, may prevent a clinician from obtaining a clear view of the larynx. In situations where intubation of a patient may be difficult, an endoscope may be used to aid visualization of the larynx and insertion of the breathing tube. An endoscope is a narrow, flexible tube that typically includes a light and camera at an insertable end of the tube and is inserted into the body for visualizing anatomical structures of a patient. The combined use of a laryngoscope and endoscope may assist the clinician in performing an intubation.

It is with respect to this general technical environment that aspects of the present technology disclosed herein have been contemplated. Furthermore, although a general environment is discussed, it should be understood that the examples described herein should not be limited to the general environment identified herein.

SUMMARY

This summary is provided to introduce a selection of concepts in a simplified form that are further described below in the Detailed Description. This summary is not intended to identify key features or essential features of the claimed subject matter.

In an aspect, the technology relates to a medical video system that includes a video laryngoscope comprising a housing, a display screen, and a processor. The system further includes a cartridge removably attached to the housing of the video laryngoscope, the cartridge comprising a port, an output drive, and first electrical contacts; and an endoscope with a proximal end having a drive system and second electrical contacts, the endoscope further having a distal end with a camera, and a pull wire connecting the drive system and the distal end such that movement of the drive system causes articulation of the distal end. The proximal end of the endoscope is sized to enter the port, align the second electrical contacts with the first electrical contacts, and engage the drive system with the output drive such that movement of the output drive causes movement of the drive system, and the processor is programmed to receive image data from the endoscope camera, display the image data on the display screen of the video laryngoscope, receive a steering input on the display screen, translate the steering input into a movement of the drive output, and transmit a steering signal to cause the movement of the output drive.

In an example, the video laryngoscope further includes a motor; and a laryngoscope output drive connected to the motor. The cartridge further includes a mechanical receiver, connected to the cartridge output drive, that mechanically couples to the laryngoscope output drive when the cartridge is coupled to the video laryngoscope. In a further example, the video laryngoscope is further programmed to, based on the steering signal, rotate the motor a direction and amount based on the steering input. In yet another example, the video laryngoscope further includes a stator portion of a motor; and the cartridge further includes a rotor portion of the motor, the rotor portion of the motor mechanically connected to the output drive, wherein, when the cartridge is coupled to the video laryngoscope, the rotor portion of the motor moves due to magnetic flux generated by the stator portion of the motor. In a further example, the video laryngoscope is further programmed to, based on the steering signal, generate a current through electromagnets of the stator portion to generate the magnetic flux. In still another example, the cartridge further comprises a motor mechanically connected to the output drive, wherein the motor operates based on the steering signal received from the video laryngoscope. In a further example, the video laryngoscope includes third electrical contacts exposed on the housing, and the video laryngoscope is further programmed to transmit the steering signal to the motor via the third electrical contacts. In still yet another example, the housing of the video laryngoscope houses the display screen, and the housing has a front surface, including the display screen, and a rear surface, wherein the laryngoscope electrical interface is positioned on the rear surface of the housing and is substantially flush with the rear surface. In a further example, the rear surface of the housing is a flat, smooth surface, and at least one of the housing or the cartridge further houses at least one retention magnet. In yet another example, the pull wire is a first pull wire and the drive system includes a drum that is connected to the first pull wire and a second pull wire, rotation of the drum in a first direction increases tension of the first pull wire and releases tension of the second pull wire; and rotation of the drum in the second direction increases tension of the second pull wire and releases tension of the first pull wire.

In another aspect, the technology relates to a medical system that includes an introducer and a cartridge. The introducer includes a proximal end including a drum connected to a pull wire; and a distal end that is steerable based on movement of the pull wire. The cartridge is attachable to a video laryngoscope and includes a first electrical interface; a port that receives the proximal end of the introducer; and an output drive that mechanically connects to the drum in the proximal end of the introducer when the proximal end of the introducer is inserted into the port. In an example, the cartridge further includes a motor mechanically connected to the output drive, the motor configured to operate based on steering signals received from the video laryngoscope when the cartridge is coupled to the video laryngoscope. In another example, the cartridge further comprises a mechanical receiver, connected to the output drive, that mechanically couples to a laryngoscope output drive when the cartridge is coupled to the video laryngoscope. In yet another example, the cartridge further comprises a rotor portion of a motor mechanically connected to the output drive, wherein, when the cartridge is coupled to the video laryngoscope, the rotor portion of the motor moves due to magnetic flux generated by a stator portion of the motor housed within the video laryngoscope. In still another example, the introducer includes a second electrical interface that couples with the first electrical interface when the proximal end is received in the port.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

DETAILED DESCRIPTION

Figure 1:
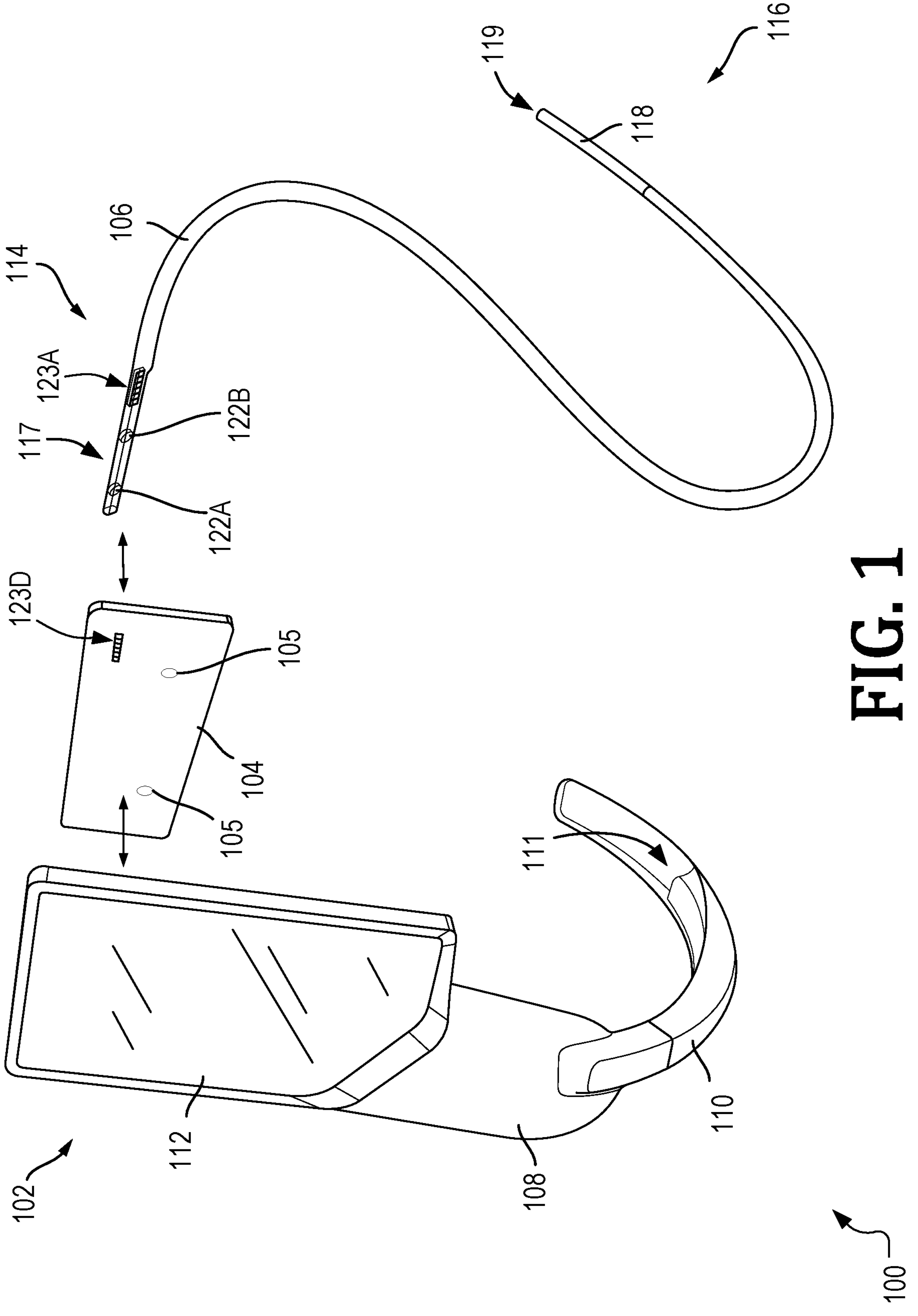
FIG. 1 depicts an example combination of a laryngoscope and an endoscope.

A laryngoscope is commonly used during the intubation of a patient who may require breathing assistance. An intubation is a medical procedure in which a clinician inserts a breathing tube (e.g., an endotracheal tube) into the mouth of the patient, past the larynx, and into the trachea. The breathing tube may then be connected to a ventilator or other device for supplying breathing gases to the patient. A laryngoscope may be used during intubation to help the clinician manipulate portions of the patient's anatomy, such as the tongue and epiglottis, and obtain a view of the larynx sufficient for inserting the breathing tube into the trachea. To further help visualize the larynx, some laryngoscopes may be configured with a video camera. A laryngoscope that includes a video camera may be referred to as a video laryngoscope (VL), and using a VL to view the larynx or other structures may be referred to as indirect-view laryngoscopy.

With some patients, performing an intubation may be difficult due to a variety of factors, such as inability to position the head or neck of the patient (e.g., due to injury), airway obstruction, atypical anatomy of the patient, other health considerations, or a combination of these or other factors. In these types of scenarios, clinicians may augment the use of a VL with a steerable endoscope, which is a narrow flexible tube that typically includes its own video camera system integrated into a steerable distal tip that is inserted into the patient's body.

The endoscope may be navigated into the airway and positioned such that it provides supplemental visualization of the airway and/or facilitates insertion of the breathing tube. In some examples, the breathing tube is passed over the endoscope and into position in the airway, with the endoscope itself serving as a channel or guide for inserting the breathing tube. When the breathing tube is placed over the endoscope prior to inserting the endoscope into the patient's airway, the breathing tube is described as being "pre-loaded" onto the endoscope. When the breathing tube is placed over the endoscope after insertion, the breathing tube is described as being "post-loaded." An endoscope used as a guide for breathing tube insertion (either pre-loaded or post-loaded) may perform the same or similar functions as an introducer and may alternatively be referred to as an introducer in some examples.

The steerable endoscope may include its own display screen as well as an external device for controlling the distal tip, such as a control stick or other type of directional controller. During intubation, it can be difficult for a single medical professional to view multiple screens and manipulate multiple devices (a video laryngoscope and endoscope) as well as an endotracheal tube.

The present disclosure describes systems and methods for a medical video system that combines a video laryngoscope and a steerable endoscope or introducer, resulting in a single instrument that may simplify and improve clinical workflows such as intubation, airway visualization, and endoscopic procedures. Examples of this instrument include a steerable endoscope that operatively couples to a detachable cartridge, which serves as an electrical and mechanical interface between the steerable endoscope and a VL, and which is detachable from the VL. In one example, the VL includes one or more electric motors that are mechanically linked through the cartridge to steering elements in the endoscope, allowing movement of the distal tip of the endoscope to be controlled by the VL. In other examples, the VL also includes an electrical interface through which electrical power is provided to the detachable cartridge and endoscope, and through which communication signals are transmitted between the VL, detachable cartridge, and steerable endoscope. For instance, power provided by the VL is received by the steerable endoscope through the detachable cartridge, and used to operate a camera, light source, sensors, and/or other electronic features of the endoscope. Video and/or sensor data from the steerable endoscope is transmitted to the VL through the detachable cartridge, via the electrical interface. A number of examples are described herein, in which elements of the present technology are distributed in different arrangements amongst the VL, detachable cartridge, and steerable endoscope.

Integrating the features of a steerable endoscope with the utility of a VL can improve clinical workflow efficiency, while providing additional benefits to clinicians. For example, the integrated device consolidates the display of video imagery from the VL and steerable endoscope onto a single screen. In addition, because the proximal end of the steerable endoscope can be disconnected from the cartridge, a clinician may easily post-load a breathing tube over the steerable endoscope. Additional details are now provided by way of discussion of the included drawings.

FIG. 1 depicts an example medical video system 100 with a VL 102 and a steerable endoscope 106. The VL 102 includes a display 112, a handle 108, and arm or extension 110, which includes a camera 111 positioned at the distal end of the arm or extension 110. The VL 102 may include additional functions or features typically associated with direct-view or indirect-view laryngoscopy, such as a power source (e.g., a battery), processor, and other electronic components.

A detachable cartridge 104 attaches to a rear side of the VL 102 and receives the proximal end 114 of the steerable endoscope 106. At the distal end 116 of the steerable endoscope 106 is a steerable tip 118 which includes one or more accessories 119. The accessories 119 may include sensors such as an inertial measurement unit (IMU), which may provide measurement data associated with the acceleration, angular velocity, position, and/or other variables associated with position/orientation/movement of the steerable tip 118 The accessories 119 may further include lights, instrument ports, and/or a camera that captures endoscope image data.

The steerable tip 118 is controlled by a drive system 117 at the proximal end 114 of the endoscope 106. In examples, the drive system 117 includes a first drum 122A and a second drum 122B. In further examples, the drums 122A-B are substantially cylindrical, with a rotational axis that is perpendicular to the long axis of the endoscope 106. Each drum 122A-B is rotatable about its axis independently of the other drum 122A-B. The drive system 117 further includes at least two pull wires connected to each of the drums 122A-B. A first pair of pull wires is connected to opposite sides of the first drum 122A and may be configured to move the steerable tip 118 in a first plane (e.g., left and right). A second pair of pull wires is connected to opposite sides of the second drum 122B and may be configured to move the steerable tip 118 in a second plane (e.g., up and down) that is substantially orthogonal to the first plane.

The pull wires are routed along the length of the steerable endoscope 106 and are connected to opposite sides of the steerable tip 118. Rotation of the first drum 122A in one direction increases tension on a first pull wire of the pair (or winds it along the drum to shorten it) and releases tension on the second pull wire of the pair (or unwinds it from the drum to lengthen it), bending the distal tip in one direction (e.g., left). Rotation of the drum 122A in the opposite direction reverses the tension/winding and bends the distal tip in the opposite direction (e.g., right). In other examples, the drums 122A-B may each be configured as a capstan, or may be associated with a capstan, where the length of a pull wire on one side of a drum 122A or B is caused to shorten, and the length of a pull wire on the opposite side is caused to extend. Accordingly, four pull wire are effectively controlled through only two drums 122A-B, which reduces the complexity of the system.

In some examples, movement of the steerable tip 118 may not be limited to rectilinear motion, and in further examples, the first and second set of axes may or may not be orthogonal to each other. In addition, one or both drums 122A-B may engage a set of one or more gears or other mechanical linkages that connect to the pull wires and translate drum rotation into movement of the steerable tip.

The proximal end 114 of the example endoscope 106 also includes an electrical interface 123A, which includes electrical contacts for receiving power and transmitting/receiving signals to/from the cartridge 104 and/or VL 102. The electrical interface 123A provides a source of input power for operating the accessories 119 (such as the sensors, cameras, light sources, and other elements described above), and/or other sensors or electronic elements included within the steerable endoscope 106.

The endoscope electrical interface 123A also provides a data path for transmitting sensor data, video images, and/or other types of data from the steerable endoscope 106 to the cartridge 104 and/or VL 102. For instance, video data captured by the camera of the endoscope 106 may be transmitted to the VL 102 via the endoscope electrical interface 123A. In some examples, signals or data (such as clock, enable, timing, and/or other signals that are used to enable communication, configure accessories, and/or perform other operational functions) may be transmitted through the electrical interface 123A in order to enable or configure the operation of the steerable endoscope 106. The electrical interface 123A may include a plurality of conductive pads, receptacles, pins, balls, ports, and/or other conductive elements used for establishing electrical connection to corresponding elements of the cartridge 104. Alternatively or additionally, wireless communication components may be incorporated into the endoscope 106 to wireless communicate data between the endoscope 106 and the VL 102 and/or cartridge 104.

The steerable endoscope 106 may be coupled to the cartridge 104 by any of a variety of methods. In one example, the endoscope 106 may slide into receiving elements of the cartridge 104 that retain the endoscope 106 to the cartridge 104. In other examples, the steerable endoscope 106 may be snap fit to the cartridge 104 or may be magnetically retained to the cartridge 104 via retention magnets 105, among other approaches. FIGS. 2-5 below illustrate example methods for coupling the steerable endoscope 106 to the cartridge 104.

When the endoscope proximal end 114 is coupled to the cartridge 104, the electrical interface 123A is conductively connected to a corresponding electrical interface of the cartridge 104, and the drums 122A-B engage one or more output drives of the cartridge 104. The drums 122A-B are driven to rotate by these output drives. To accomplish this transmission of force, the drums 122A-B and the cartridge include a mating interface with mating mechanical features. For instance, the drums 122A-B may include edges, shaped surfaces, corners, prongs, notches, studs, teeth, cogs, protrusions, and/or other features that engage with (and receive rotational force from) complementary or mating features on the cartridge output drives. The cartridge output drives may be any of a variety of mechanical features suitable for coupling rotational force to the drums 122A-B. For example, the cartridge output drives may include one or more hubs, axles, gears, rods, spindles, sprockets, couplings, linkages, and/or other types of mechanical elements. These elements may include force-transmitting features such as edges, surfaces, corners, prongs, notches, studs, teeth, cogs, protrusions, and/or other physical or mechanical features that engage counterposing, force-receiving features of the drums 122A-B and transmit rotational force. In examples, the cartridge output drives and/or drums 122A-B may include alignment features, such as guides, slots, chamfers, bevels, and/or other features that automatically cause the force-transmitting features of the drives 122A-B to align and engage force-receiving features of the drums 122A-B, when the endoscope proximal end 114 is brought into contact (connected) with the cartridge 104.

When the cartridge 104 is coupled to the VL 102, the VL 102 provides control of the endoscope steerable tip 118 through the cartridge 104. FIGS. 2-5 below depict several example systems in which a VL may provide steering control of the endoscope steerable tip 118 via the cartridge 104.

The cartridge 104 also includes a cartridge-VL electrical interface 123D (similar to electrical interface 123A) that connects to an electrical interface on the VL 102 (depicted in later examples). The cartridge 104 may act as an electrical passthrough between the VL 102 and steerable endoscope 106, allowing the VL 102 to distribute power to the steerable endoscope 106 and allowing for bidirectional data transmission between the VL 102 and steerable endoscope 106.

In an example, the VL 102 receives data (such as video images) from the steerable endoscope 106 through the cartridge 104 and displays the received data on the display 112. The display may be capable of displaying images from multiple cameras simultaneously, such as images from the VL camera 111 and the endoscope camera, such as by split screen, picture-in-picture, or other display methods. The display 112 may be any of a variety of display technologies, such as LCD, LED, OLED, or other display technology. In examples, the display 112 may be a touch-sensitive display (e.g., a capacitive touch-sensitive display) that allows user input to be received through the display 112. Further, the display 112 may receive steering inputs from a user of the VL 102 for control of the endoscope steerable tip 118, or in some examples, the user may provide steering inputs via input keys or buttons associated with the VL 102. Elements of the VL 102 may translate the control inputs to corresponding motor outputs, which are transmitted to the drums 122A-B through the cartridge 104 for control of the steerable tip 118.

The VL 102, cartridge 104, and steerable endoscope 106 may be connected/disconnected in any order at any time during operation. For example, in operation, a clinician may prefer to post-load a breathing tube over the steerable endoscope 106. The endoscope steerable tip 118 may be guided into a preferred position in the patient airway, and the endoscope proximal end 114 disconnected from the cartridge 104. A breathing tube (such as an endotracheal tube) may then be post-loaded over the steerable endoscope 106, and the proximal end 114 re-inserted into the cartridge 104. During this post-loading, the cartridge 104 can remain attached to the VL or can be detached and re-attached as needed.

The VL 102 may be capable of detecting the presence/absence of the cartridge 104 and/or steerable endoscope 106 (or vice versa). When detected, the VL 102 may energize power and signal connections to the cartridge 104 and/or steerable endoscope 106. In one example, the cartridge 104 and/or steerable endoscope 106 includes a magnetic element, and the VL 102 includes a sensor capable of detecting the magnetic element (such as a Hall effect sensor).

The cartridge 104 may be coupled to the VL 102. In one example, the cartridge 104 and/or VL 102 includes one or more permanent magnets that align and retain the cartridge 104 to the VL 102. Magnetic retention can be accomplished with smooth surfaces (without sharp edges, grooves, etc.) which is beneficial for avoiding dirt/containment traps and enabling easy cleaning of the devices between uses. In other examples, the cartridge 104 is aligned and retained to the VL 102 by other methods, such as by spring retention elements, clips, and/or other types of retention elements. The VL 102 and/or cartridge 104 may include alignment and/or retention features, such as guides, rails, notches, posts, and/or other physical features that facilitate alignment and retention of the cartridge 104 to the VL 102.

Removing and reconnecting the cartridge 104 and/or steerable endoscope 106, such as to post-load a breathing tube, may increase the risk of exposing the VL 102 to bio-contaminants. For example, when the steerable endoscope 106 is re-inserted into the cartridge 104 following the post-load procedure, any bio-contaminants that may be present on the endoscope proximal end 114 (as a result of the post-load procedure) may be imparted to surfaces of the VL 102. Additionally or alternatively, any dirt or contaminants that may be present on the surface of the VL 102 may be imparted onto the endoscope proximal end 114 as the proximal end 114 is connected/disconnected from the cartridge 104. These contaminants may further be passed to the patient as the breathing tube is post-loaded and guided into the airway. Therefore, the coupling method used to retain the cartridge 104 to the VL 102, along with elements of the electrical and mechanical interfaces (as applicable), may be designed with minimal edges or other physical features that may be prone to trapping dirt or contaminants, and/or the VL 102 may further be designed to be easily and thoroughly cleaned. In some examples, the cartridge 104 and steerable endoscope 106 may be treated as one-time use or disposable. For instance, the cartridge 104 and steerable endoscope 106 may be sealed and packaged together for one-time use, while the VL 102 may be cleaned for re-use. In examples where the cartridge 104 and/or VL 102 have been designed to reduce cross-contamination, the cartridge 104 may further help reduce contamination following breathing tube post loading. For example, the cartridge may serve as a barrier between the steerable endoscope 106 and VL 102, preventing any contaminants from being transmitted between the steerable endoscope 106 and VL 102.

In examples, elements and features of the example video system 100 described above may be distributed in a number of possible arrangements. FIGS. 2-5 present additional example systems that depict additional steering control approaches. FIG. 7 provides system block diagrams that further depict how elements of example systems may be distributed between the VL 102, cartridge 104, and steerable endoscope 106.

Figure 2B:
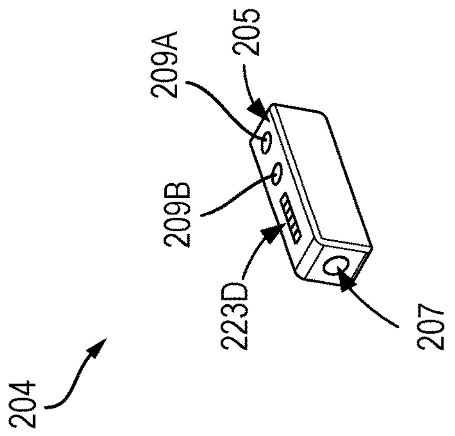
FIG. 2B depicts a bottom perspective view of an example detachable cartridge.
Figure 2A:
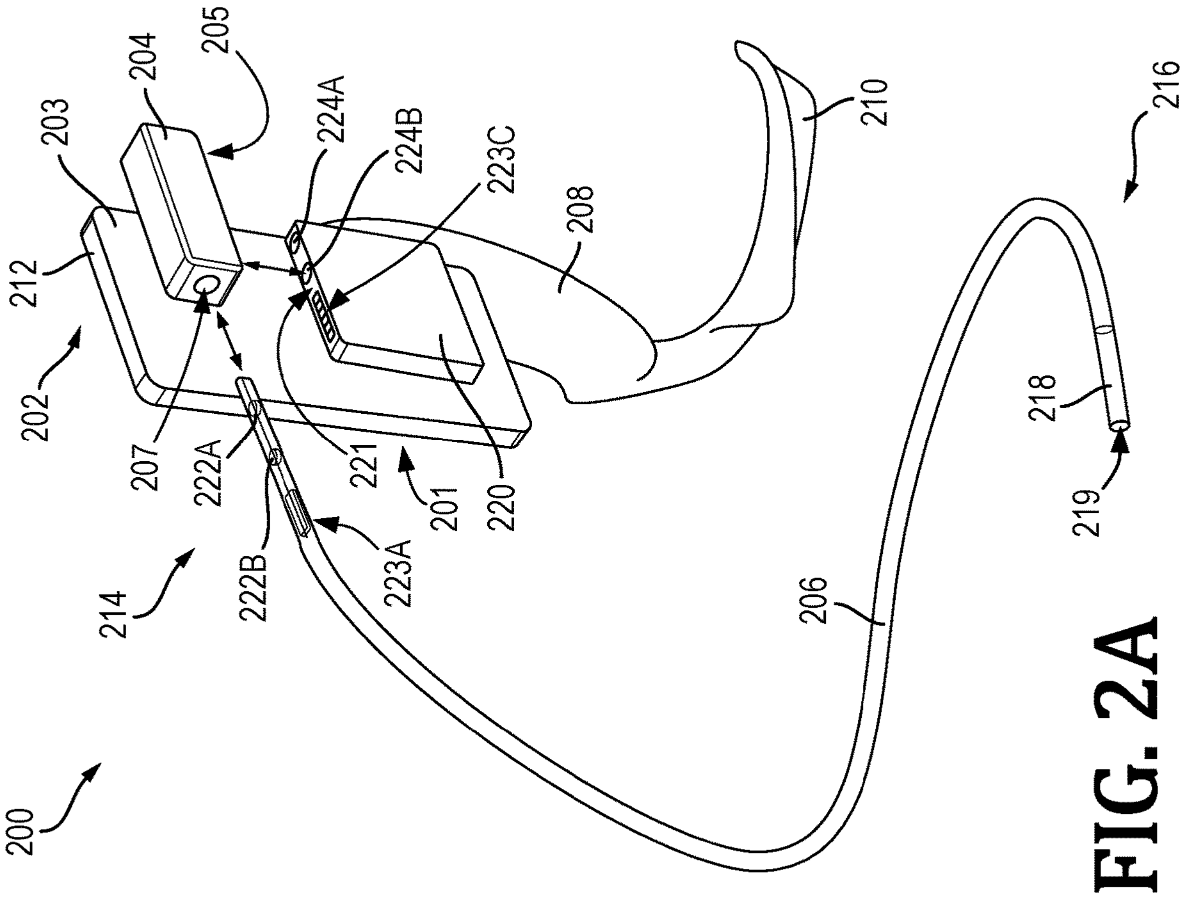
FIG. 2A depicts another example combination of a laryngoscope and an endoscope.

FIG. 2A depicts a rear view of another example video system 200, and FIG. 2B depicts a bottom view of an example cartridge 204. In this embodiment, the system 200 includes a drive housing 220 that imparts rotational force to the cartridge 204. In the example video system 200, a VL 202 is couplable to a steerable endoscope 206 via cartridge 204, which, when coupled to the VL 202, comes into contact with, and engages, a drive housing 220. As described in further detail below, the drive housing 220 includes elements that impart rotational force to elements of the cartridge 204, for control of the endoscope steerable tip 218 by the VL 202. The VL 202 also includes a handle 208, blade 210, and display 212, which may be similar to, or the same as, corresponding elements described in FIG. 1.

The display 212 may be positioned within a housing that has a front surface 201 and an opposite rear surface 203. The display screen of the display 212 is on the front surface 201 and additional features of the technology discussed herein may be positioned on the rear surface of the display housing.

In the example depicted in FIG. 2, the rear surface 203 of the housing of the display 212 includes the drive housing 220, which may be in the form of a protruding compartment and include elements such as motors, gear boxes, transformers, drive chains, etc. The elements within the drive housing 220 (e.g., motors) generate mechanical force that is applied to the cartridge 204 to steer the endoscope 206. A surface (e.g., the top surface 221) of the drive housing 220 includes an electrical interface 223C and VL output drives that transmit rotational force from the drive housing 220 to the cartridge 204. In this example, the VL output drives include a first hub 224A, and a second hub 224B). In other examples, the VL output drives may include one or more axles, gears, rods, spindles, sprockets, couplings, linkages, and/or other types of mechanical elements suitable for engaging the mechanical receivers 209A-B of the cartridge 204, and transmitting rotational force from the VL 202 to the mechanical receivers 209A-B.

The hubs 224A-B are connected to electric motors housed within the drive housing 220 or elsewhere in the VL 202. The motors may be a type of DC motor, such as servo motors, stepper motors, or other type of DC motor, or in some examples may be a type of AC motor. The motors may receive power from the VL power source, such as from one or more batteries or from power supply elements or components that receive power from the battery(ies). Rotation of the motor axles causes rotation of the hubs 224A-B, which transmit steering forces generated by the motors through the cartridge 204 to the steerable endoscope 206. In examples where each of the drums 222A-B controls bidirectional movement of the endoscope steerable tip 218 in a plane, a single motor of the VL 202 may provide independent bidirectional control of the endoscope steerable tip 218 within that plane. The steerable tip 218 may include accessories 219, such as sensors, one or more cameras, lights, etc., that are similar to, or the same as, accessories 119 described above for FIG. 1.

Hubs 224A-B include features (such as edges, surfaces, corners, prongs, notches, studs, teeth, cogs, protrusions, or other physical or mechanical features) that engage and impart rotation to corresponding features of the cartridge mechanical receivers 209A-B (FIG. 2B), when the cartridge 204 is coupled to the VL 202. The input mechanical receivers 209A-B the cartridge 204 may include drums, axles, spindles, or other types of mechanical receptacles (including non-rotational elements) capable of receiving rotational force from the hubs 224A-B. In examples, the hubs 224A-B and/or corresponding cartridge mechanical receivers 209A-B may include additional features that automatically align the hubs 224A-B and cartridge mechanical receivers as the cartridge 204 is coupled to the VL 202.

The VL 202 also includes an electrical interface 223C that includes a set of conductive elements for providing power to the cartridge 204 and endoscope 206 and for allowing communication signals to be transmitted/received to/from the VL 202. The cartridge bottom surface 205 (FIG. 2B) includes a corresponding cartridge-VL electrical interface 223D that mates with the electrical interface 223C. In examples, elements of the electrical interfaces 223C-D may be similar to, or the same as, electrical interface 123A depicted in FIG. 1.

As described, the cartridge 204 includes mechanical receivers 209A-B that correspond and couple to each of the hubs 224A-B. The steering forces generated by the motors of the VL 102 are applied to the cartridge mechanical receivers 209A-B, which transmit the steering forces to one or more cartridge output drives housed within the cartridge 204. The cartridge output drives may include rotational elements such as hubs, axles, gears, rods, spindles, sprockets, couplings, linkages, and/or other types of mechanical output elements (including non-rotational elements). The cartridge mechanical receivers 209A-B and output drives may be connected to one another, internally to the cartridge 204, by gears, axles, linkages, and/or other methods of mechanical connection.

The cartridge 204 also includes a cartridge-endoscope electrical interface for making electrical connection with the endoscope electrical interface 223A. The cartridge-VL electrical interface 223D and cartridge-endoscope electrical interface may be connected within the cartridge 204 by any of a variety of methods for electrical connection, such as wires, rigid or flexible pins, flexible (flex) printed circuits, rigid or rigid-flex printed circuit boards (PCBs), and/or other methods of establishing electrical connection.

The cartridge 204 further includes an endoscope port 207 that receives the endoscope proximal end 214. The cartridge 204 may be designed to allow the endoscope 206 to be inserted into the endoscope port 207 at a depth that results in alignment of the electrical and mechanical interface elements of the endoscope 206 with corresponding elements of the cartridge 204. For instance, the endoscope port 207 may include a mechanical stop that blocks further insertion of the endoscope 206 when the first and second drums 222A-B are aligned with corresponding cartridge output drives, and the electrical interface 223A is aligned with the cartridge-endoscope electrical interface. Another example is rails or protrusions that guide the endoscope into the port 207. When the proximal end 214 of the endoscope 206 is inserted into the endoscope port 207 to an extent that properly aligns corresponding electrical/mechanical elements of the steerable endoscope 206 and cartridge 204, the steerable endoscope 206 may be considered to be in a fully inserted position.

The endoscope 206 may also have similar features as those described above, such as the proximal end 214, a distal end 216, a steerable tip 218, and an accessory interface or camera 219. The endoscope proximal end 214 may include additional features that interact with and engage counter-facing features of the cartridge 204 to further cause or ensure alignment between mechanical and/or electrical elements of the endoscope proximal end 214 with corresponding mechanical and/or electrical elements of the cartridge 204. In one example, the endoscope proximal end 214 may include one or more rails or protrusions, and the cartridge 204 may include one or more guides for receiving the rail(s) or protrusion(s). The guide(s) may permit insertion of the endoscope proximal end 214 when the rail(s) are aligned with the guide(s), such that mechanical and electrical elements of the cartridge 204 and steerable endoscope 206 are caused to face each other. Full insertion of the endoscope proximal end 214 thereby causes alignment of the mechanical and electrical elements of the cartridge 204 and endoscope 206. In another example, the shape of the endoscope proximal end 214 (such as an asymmetric cross-sectional shape), and/or the shape of elements or features of the endoscope port 207 and/or cartridge 204 may be designed to allow insertion of the endoscope proximal end 214 in only one orientation, which properly aligns the interfaces.

In examples, the cartridge 204 includes a feature that retains the proximal end 214 of the endoscope 206, when fully inserted into the endoscope port 207, such as with internal springs, clips, or other elements that apply force to portions of the proximal end 214 to retain it against a removal force.

The cartridge 204 may further include an external element that applies retention force to the endoscope proximal end 214, such as a push-button, knob, lever, or other mechanical element. In some examples, the cartridge 204 may include a visual indication that the proximal end 214 is retained within the endoscope port 207. For instance, the cartridge 204 may provide a "locked" symbol, may activate a visible light source (such as an LED or other light source), or may provide some other type of indication that the steerable endoscope is connected and retained within the cartridge 204.

The cartridge 204 is held in position against the drive housing 220 such that hubs 224A-B sufficiently engage the cartridge mechanical receivers 209A-B so that force may be transferred from the hubs 224A-B to the mechanical receivers 209A-B and to make electrical contact between electrical interfaces 223C-D. In one example, the cartridge 204 is secured to the VL 202 by one or more retention magnets located in the cartridge 204 and/or the VL 202. In other examples, other methods may be used to retain the cartridge 204, such as spring retention elements, guides, rails, posts, and/or other mechanical elements suitable for retaining the cartridge 204 to the VL 202. These retention elements may be located in the cartridge 204 and/or in the VL 202, such as in the drive housing 220 or the housing of the display.

In operation, the steerable endoscope 206 is inserted into the endoscope port 207 of the cartridge 204. The steerable endoscope 206 may be pre-loaded with a breathing tube, or the breathing tube may be post-loaded.

The cartridge 204 is coupled to the VL 202. An endoscope video camera receives power from the VL 202 and returns video data through the electrical interface 223A. A position sensor (or other sensors or accessories) mounted in the endoscope steerable tip 218 may also receive power and return data over the electrical interface 223A. Video and positional sensor data may be transmitted to the VL 202 and shown on the display 212 to assist a clinician in guiding the endoscope distal end 216 into the desired position in the airway.

During use, the clinician may control the endoscope steerable tip 218 by providing touch inputs via display 212. The VL 202 translates these steering inputs into rotation of the hubs 224A-B, which in turn drive the cartridge mechanical receivers 209A-B, which are coupled to the drums 222A-B of the endoscope 206. Rotation of the drums 222A-B causes movement of internal pull wires, which in turn direct the movement of the endoscope steerable tip 218. Once the endoscope steerable tip 218 is positioned in the airway, if appropriate, the clinician may complete the intubation and post-load the endoscope. Touch inputs from the operation via the VL screen 212 may then be received to cause active steering of the distal tip 218 of the endoscope as well as control operations of the VL 202. Accordingly, as compared to other systems, a single operator (e.g., clinician) may control both the video laryngoscope and endoscope without needing the assistance of another person to hold or guide the endoscope and/or a separate control system for the endoscope.

During an intubation the VL 202, cartridge 204, and steerable endoscope 206 may be coupled/decoupled from one another at any time, in any order. In one example, the steerable endoscope 206 may be removed from the cartridge 204 in order to post-load a breathing tube, while the cartridge 204 remains coupled to the VL 202. The steerable endoscope 206 may be reinserted into the cartridge 204 following the post-load procedure. In another example, the cartridge 204 may be decoupled from the VL 202 while the steerable endoscope 206 remains coupled to the cartridge 204.

Figure 3:
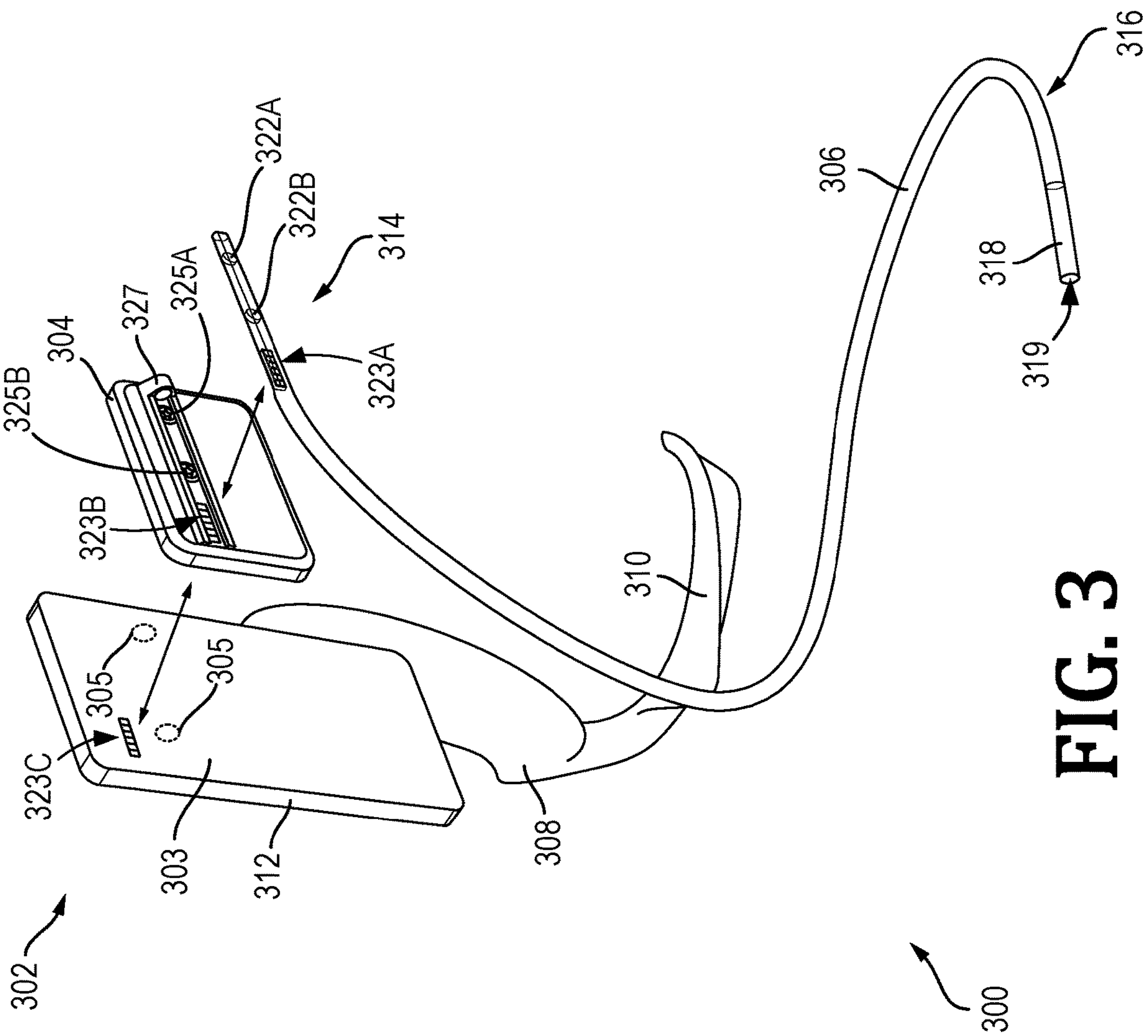
FIG. 3 depicts another example combination of a laryngoscope and an endoscope.

FIG. 3 depicts a rear view of another example video system 300, in which a steerable endoscope 306 is connected to a VL 302, via cartridge 304. The VL 302 may have some features/functions that are similar to, or the same as, example VL 102 and/or VL 202 described in FIGS. 1 and 2, such as a handle 308, blade 310, and display 312. The endoscope 306 may also have similar features as those described above, such as a proximal end 314, a distal end 316, a steerable tip 318, and accessories 319. However, rather than exerting steering forces through mechanical coupling, as in the example depicted in FIG. 2, the VL 302 exerts steering control by inductively coupling steering forces to the cartridge 304, which applies the forces to the endoscope drums 322A-B.

For example, the VL 302 may include one or more stationary electromagnetic elements that generate electromagnetic fields that inductively couple to one or more rotational electromagnetic elements in the cartridge 304. The electromagnetic elements included in the VL 302 and cartridge 304 may include one or more coiled conductors (e.g., coils) wound in any of a wide variety of shapes and configurations.

In some examples, the electromagnetic elements of the VL 302 and cartridge 304 may be arranged to form an electric motor that spans the VL 302 and cartridge 304. For instance, the stationary electromagnetic elements of the VL 302 may be arranged to form the stator of a motor, and the rotational electromagnetic elements of the cartridge 304 may be arranged to form a rotor. In one example, the electromagnetic elements of the VL 302 and cartridge 304 may form an axial electric motor. An axial motor is a type of electric motor where the magnetic flux between the stator and rotor is primarily aligned parallel to the axis of rotation of the rotor, rather than radially, as in other types of motors. Additional details of how an axial motor may be implemented in an example video system are provided in FIGS. 4A-4B and the accompanying description.

The cartridge 304 may include one or more rotors that are mechanically connected to cartridge output drives, which couple to the endoscope drums 322A-B. In example video system 300, the cartridge output drives are implemented as a first cartridge hub 325A and a second cartridge hub 325B. In other examples, the cartridge output drives may be implemented as one or more axles, rods, spindles, sockets, and/or other types of mechanical elements suitable for transmitting rotational force.

Within the cartridge 304, the rotors are connected to the cartridge hubs 325A-B, which include features (such as edges, surface, prongs, notches, teeth, protrusions, etc.) that engage the drums 322A-B, and transmit rotational force to the drums 322A-B. The cartridge hubs 325A-B may further include features (such as guides, slots, chamfers, bevels, etc.) that automatically align the drums 322A-B to the cartridge hubs 325A-B as the endoscope 306 is coupled to the cartridge 304.

The endoscope proximal end 314 is coupled to the cartridge 304 via the guide 327. In examples, the endoscope proximal end 314 may slide into one end of the guide 327 and abut a mechanical stop at the end of the guide 327 (i.e., the steerable endoscope 306 is fully inserted), which aligns the drums 322A-B with the cartridge hubs 325A-B and aligns the endoscope electrical interface 323A with the cartridge-endoscope electrical interface 323B. Features of the endoscope retention guide 327, such as rails, rims, and/or other features, may apply a retention force to the endoscope proximal end 314 to establish and maintain coupling between the endoscope 306 and cartridge 304. Features of the retention guide 327 and/or endoscope proximal end 314 may allow insertion of the endoscope proximal end 314 in only one orientation to prevent incorrect insertion (such as by the methods described for FIG. 2). When the endoscope 306 is fully inserted into the endoscope retention guide 327, the applied retention force causes the drums 322A-B to mechanically engage the cartridge hubs 325A-B, and elements of the endoscope electrical interface 323A to make electrical contact with elements of the cartridge-endoscope electrical interface 323B.

In the embodiment of FIG. 3, the cartridge 304 is coupled to the rear surface 303 of the VL 302 by retention magnets 305 housed within the cartridge 304 and/or VL 302. For instance, the retention magnets 305 are housed within the display housing of the VL 302 and/or in the cartridge 304. The retention magnets 305 apply sufficient force to retain the cartridge 304 against the rear surface 303 while the VL 302 and endoscope 306 are in use, while allowing the cartridge 304 to be removed as needed during intubation.

The force applied by the retention magnets 305 to retain the cartridge 304 to the rear surface 303 may also align the cartridge 304 with electrical and mechanical elements of the VL 302. In examples where the electromagnetic elements form an axial motor, the force produced by the retention magnets may align the stator of the VL 302 with the rotor of the cartridge 304, thereby enabling transmission of energy for steering control of the endoscope steerable tip 318 through the cartridge 304. For instance, one or more retention magnets 305 of the VL 302 and/or one or more retention magnets 305 in the cartridge 304 may be positioned such that when the cartridge 304 is coupled to the VL 302, the cartridge is retained in a position where the stator portion of the motor in the VL 302 is aligned with the rotor portion of the motor in the cartridge 304 are aligned.

The rear surface 303 of the cartridge 304 also includes a cartridge-VL electrical interface that makes electrical contact with the VL electrical interface 323C when the cartridge 304 is coupled to the VL 302. The force applied by the retention magnets 305 may also cause alignment and contact between elements of the cartridge-VL electrical interface and elements of the VL electrical interface 323C. The elements of electrical interfaces 323A-C, and the cartridge-VL electrical interface, may be similar to, or the same as, elements of electrical interfaces described above (such as electrical interfaces 123A and 223A,C).

By having the moving components of motors (e.g., the stator portions) housed within the cartridge 304, rather than the video laryngoscope 302, the rear surface 303 of the display housing can be smooth and/or flat to help prevent the trapping of dirt or contaminants in crevices or other physical ports, holes, etc. In addition, the VL electrical interface 323C may be substantially flush with the rear surface 303 to again help prevent trapping of dirt or contaminants within the or around the video VL electrical interface 323C. Accordingly, the VL 302 may be more easily cleaned or disinfected. In addition, by including the moving components of the motors in the cartridge 304, rather than the VL 302, the reliability and longevity of the VL 302 may be improved because moving parts are more prone to deterioration, fatigue, or other reliability concerns over time.

Aspects of the operation of example video laryngoscope system 300 may be substantially similar to or the same as the operations described for example video laryngoscope system 200.

Figure 4B:
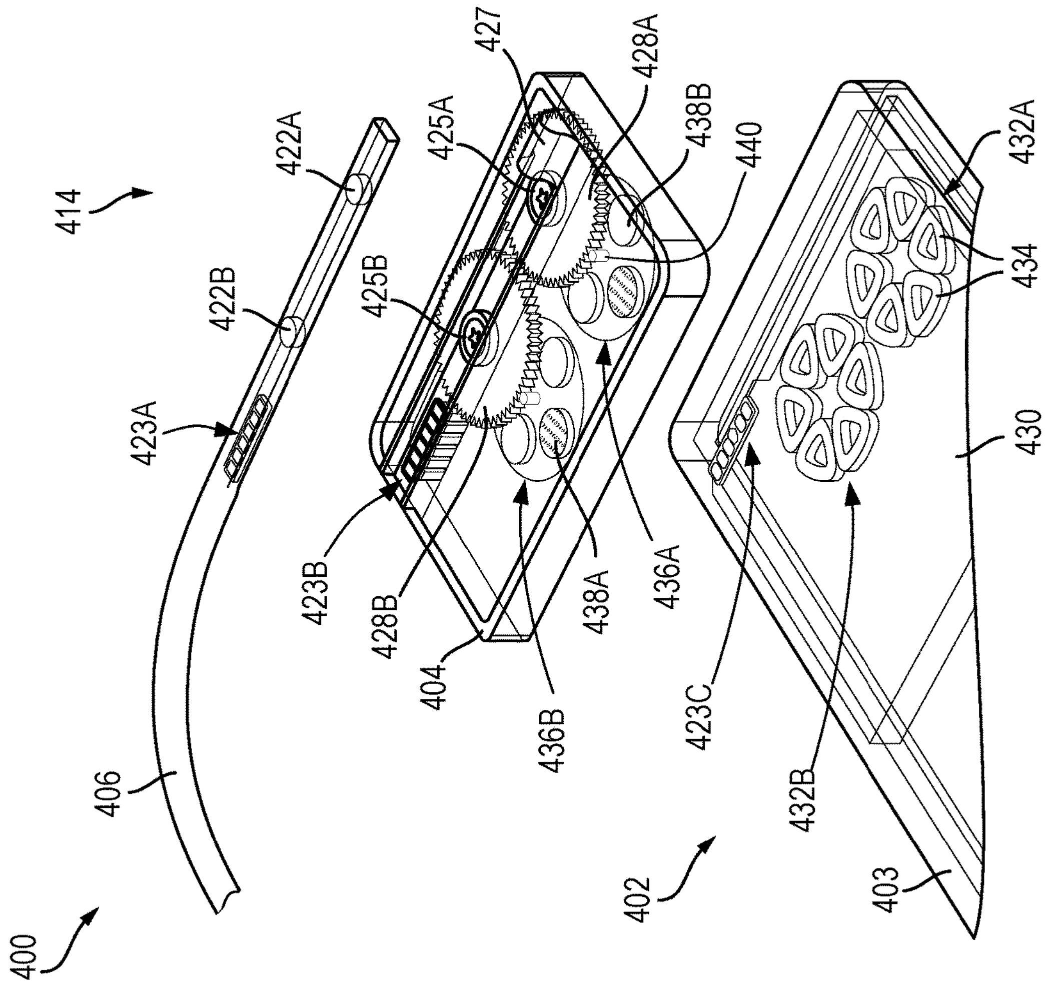
FIG. 4B depicts an example combination of a laryngoscope and an endoscope.
Figure 4A:
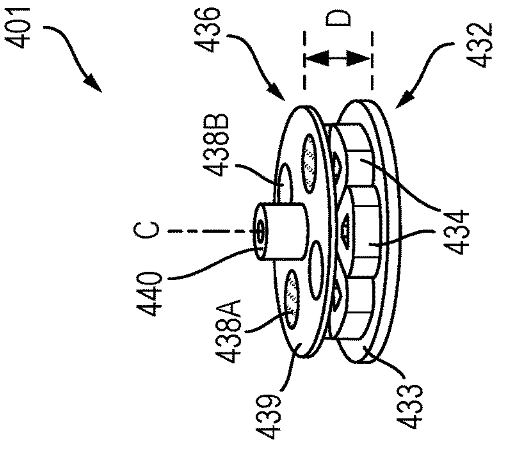
FIG. 4A depicts a detailed view of an example axial motor.

FIG. 4A depicts a detailed view of an example axial motor 401, and FIG. 4B depicts an example video system 400, where an axial motor is used for providing steering control of the endoscope steerable tip. The example axial motor 401 includes a stator 432 and a rotor 436. The stator 432 includes a plurality of electromagnets 434, which may each include a number of turns of a coiled conductor (e.g., coils) wound with a particular shape. In some examples, the coils of the electromagnets 434 may each be wound around a core element having defined ferromagnetic properties (such as a permanent magnet, iron, etc.), while in other examples, the electromagnets 434 may not include a core element. The design and arrangement of electromagnets 434 may be at least partially based on a target axial motor performance parameter such torque, speed, and/or other performance parameters or design factors. The electromagnets 434 are mounted to a stator frame 433 and arranged circumferentially around a central axis of rotation C that is common to both the stator 432 and rotor 436.

The rotor 436 includes a number of magnetic elements 438A-B that are mounted to a rotor frame 439 and arranged with alternating polarities. For instance, magnetic element 438A may be arranged with a North-South (N-S) polarity, where the axis of polarity is parallel to the central axis C, and magnetic element 438B may be arranged with a S-N polarity. Remaining magnetic elements may be arranged in a pattern of alternating polarities, or in some examples, may be arranged according to another pattern or arrangement methodology. The rotor 436 may further include a rotor axle 440, which may couple to mechanical elements associated with the rotor.

The principles of operation of example axial motor 401 may be the same as or identical to the general principles of operation of many other types of electric motors. Briefly, the electromagnets 434 may be connected to a source of controlled electrical current that energizes the electromagnets 434 in such a way that the magnetic fields/flux generated by the electromagnets 434 cause force to be applied to the magnets 438A-B. This applied force results in rotation of the rotor 436 about the central axis of rotation C. During operation, the stator 432 and its associated electromagnets 434 remain stationary.

Although the rotor 436 and stator 432 share a common central axis of rotation C, in some examples, the rotor 436 or elements of the rotor 436 may not be in physical contact with the stator 432 or elements thereof. Although not depicted in FIG. 4A, the rotor 436 may be associated with elements that fix the distance between the rotor 436 and the stator 432 and provide mechanical support to the rotor 436, while allowing the rotor 436 to rotate freely and independently of the stator 432. The distance between the rotor 436 and stator 432 is indicated in FIG. 4A by the parameter D. As an example, distance D between the rotor 436 and stator 432 may be increased, but magnetic flux generated by the stator 432 may still result in rotation of the rotor 436. In some examples, the distance D may be large enough that intervening material(s) may be placed between the rotor 436 and stator 432, and the example axial motor 401 may still operate as intended. For instance, the rotor 436 may be placed in the cartridge 404 and the stator 432 may be placed in the VL 402, where the intervening material may be the housing of each device.

FIG. 4B depicts an exploded view of an example video system 400 that incorporates an axial motor, where the stator 432 is housed in the VL 402, and the rotor 436 is housed in the cartridge 404. Aspects of the example VL system 400 may be similar to, or the same as, example video laryngoscope system 300 depicted in FIG. 3 and described above.

As depicted in FIG. 4B, the VL 402 includes a motor subsystem 430, which houses a pair of stators 432A-B, each comprising a plurality of electromagnets 434. In this example the electromagnets 434 do not include core materials, but in other examples the electromagnets 434 may include core materials. The motor subsystem 430 may include elements for controlling a source of electrical current used to energize the electromagnets 434. For example, the motor subsystem 430 may include analog or digital circuitry, power supply elements, one or more processors (e.g., microcontrollers, programmable logic, etc.), and/or other elements capable of, or associated with, controlling the current through electromagnets 434 of stators 432A-B. In some examples, the motor subsystem 430 may include elements associated with converting steering control inputs (such as from a touch-sensitive display of the VL 402) to corresponding stator output (such as electrical current sourced to the electromagnets 434) for controlling the endoscope steerable tip (depicted in previous figures).

The cartridge 404 includes two rotors 436A-B, each with a plurality of magnetic elements. As described in FIG. 4A, neighboring magnetic elements may be arranged in the rotor 436 with alternating polarities, such as magnetic elements 438A with a first polarity (e.g., N-S) positioned adjacent to magnetic elements 438B with the opposite polarity (e.g., S-N). The rotors 436A-B include rotor axles 440, which serve as central axes of rotation. In examples, the rotor axles 440 may be toothed, geared, notched, or may otherwise have physical features that engage similar features of a first and second gear 428A-B. The gears 428A-B include first and second cartridge hubs 425A-B, respectively. In this example, the cartridge hubs 425A-B serve as cartridge output drives.

As described above, and depicted in FIG. 3, the endoscope proximal end 414 may be fully inserted into guide 427, wherein the first and second drums 422A-B align with, and couple to, respective cartridge hubs 425A-B. Each of the drums 422A-B is associated with a pair of pull wires for bidirectional control of the endoscope steerable tip.

The cartridge 404 may be coupled to the VL rear surface 403 by retention magnets (not depicted) or other methods, which position the rotors 436A-B in sufficient proximity to the stators 432A-B to form an operable axial motor. Steering control inputs from a user are converted to corresponding magnetic flux generated by the stators 432A-B, which causes corresponding rotation of one or more of the rotors 436A-B. Rotation of one or both rotors 436A-B causes rotation of one or both of the corresponding cartridge hubs 425A-B via rotation of the associated gears 428A-B, respectively. In the example video system 400, one axial motor (i.e., one stator and one corresponding rotor) provides steering control for each of the drums 422A-B. Thus, each axial motor controls bidirectional movement of the endoscope steerable tip within a plane.

Electrical interfaces similar to the interfaces described above may also be included in the system 400. For instance, the cartridge 404 includes a cartridge-endoscope electrical interface 323B that contacts an endoscope electrical interface 423A when the endoscope 406 is attached to the cartridge 404. The VL 402 includes a VL-cartridge electrical interface 423C that contacts a cartridge-VL electrical interface of the cartridge 404 when the cartridge is coupled to the VL 402.

Figure 5B:
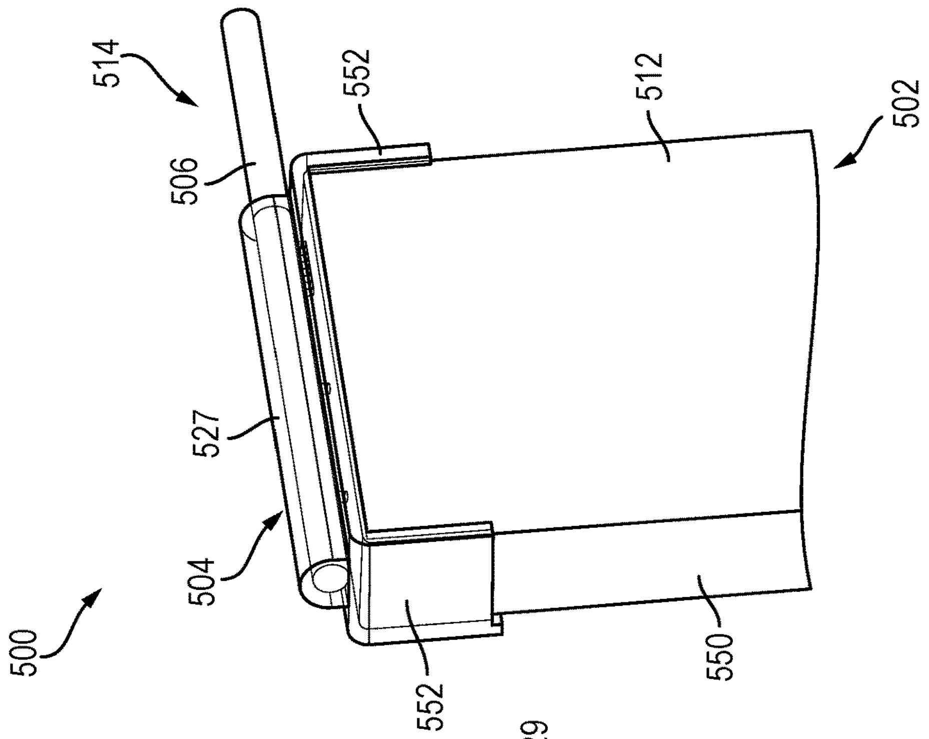
FIGS. 5A-5B depict views of another example combination of a laryngoscope and an endoscope.
Figure 5A:
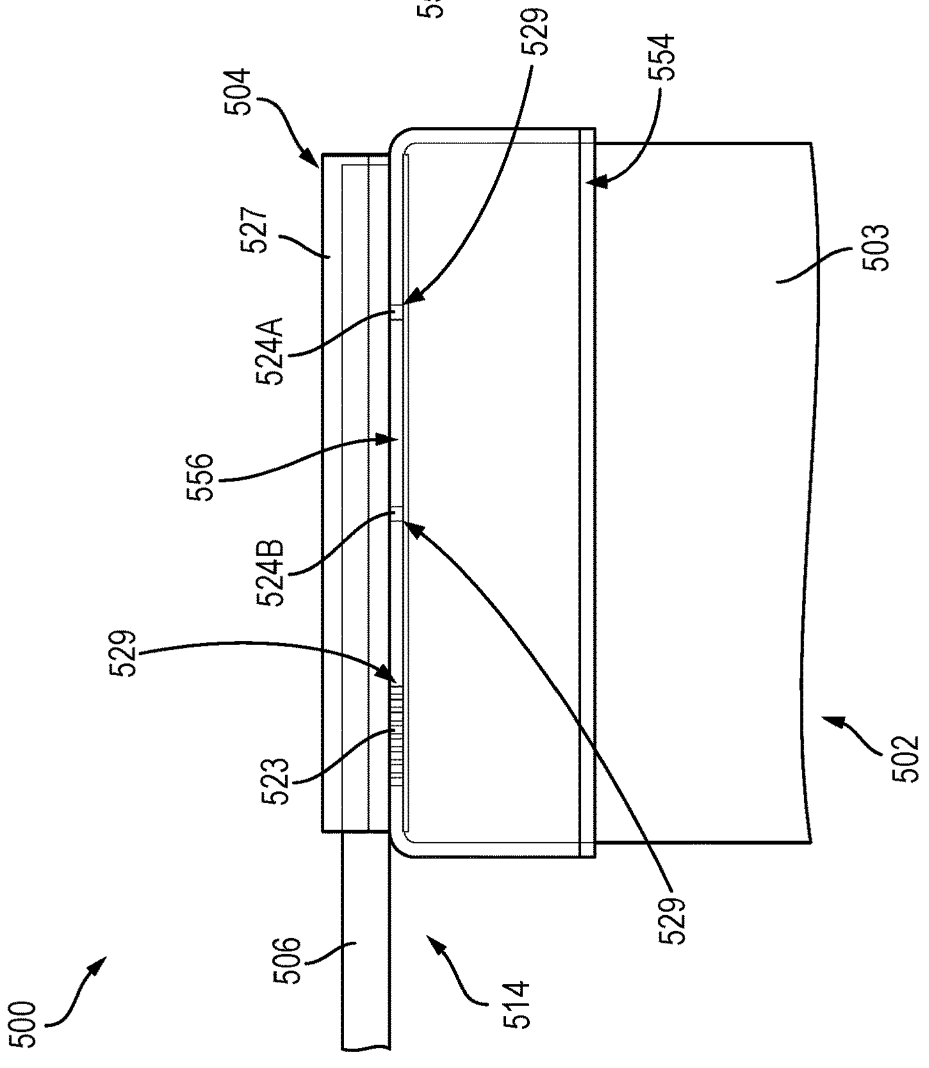

FIG. 5A-5B depict views of another example video system 500 with a steerable endoscope 506 connected, where a slim cartridge 504 allows direct interaction between steering control elements of the VL 502 and steerable endoscope 506. The example cartridge 504 includes two side retainers 552 and a back retainer 554, which apply retention forces to the side surfaces 550 and rear surface 503 of the VL 502. For instance, the two side retainers 552 and the back retainer 554 are shaped based on the size of the display housing of the VL 502. The retention forces maintain coupling between the cartridge 504 and VL 502.

When the cartridge 504 and steerable endoscope 506 are coupled to the VL 502, one or more actuators (such as motors or other elements) in the VL 502 extend impingement rod sets 524A-B through sealed cartridge apertures 529 of cartridge top interface surface 556. In some examples, the actuator(s) further extend impingement rod sets 524A-B through sealed apertures in the steerable endoscope 506 and into the interior of steerable endoscope 506, where the impingement rod sets 524A-B engage mechanical elements that provide steering control of the endoscope steerable tip. In one example, the first impingement rod set 524A and second impingement rod set 524B each include a single impingement rod that engages a corresponding steering element (such as a rotational or other type of element). A single impingement rod may provide control of the endoscope steerable tip along one or more axes by rotation (as described in previous examples) or by another method of mechanical actuation.

In other examples, the first impingement rod set 524A and second impingement rod set 524B may each include two or more impingement rods, which may enable linear steering control. For example, a pair of impingement rods of each impingement rod set 524A or 524B may each directly or indirectly impinge on a pull wire of a pull wire pair in the steerable endoscope 506. Each impingement rod of a pair may work in opposition, with one impingement rod causing shortening of one of the pull wires, and the other (opposing) impingement rod causing lengthening of the remaining pull wire of the pull wire pair. In this regard, the impingement rod pair enables steering control of the endoscope steerable tip along one or more axes. In this example, the remaining pair of impingement rods provides similar steering control along one or more additional axes through interaction with another pair of pull wires.

Within the VL 502, impingement rod sets 524A-B are connected to motors, gears, axles, linkages, and/or other actuators which cause rotation, translation, and/or other forms of mechanical actuation for providing control of the endoscope steerable tip. In some examples, a first set one or more actuators may cause extension of the impingement rod sets 524A-B through the sealed cartridge apertures 529 and through apertures of the steerable endoscope 506, while a second set of one or more actuators cause actuation of the impingement rod sets 524A-B for providing control of the endoscope steerable tip.

The cartridge 504 also includes an electrical interface for establishing electrical contact between the VL 502 and endoscope 506. For example, actuators (such as motors or other elements) in the VL 502 may extend conductive elements 523 through sealed cartridge apertures 529 of cartridge top interface surface 556. The conductive elements 523 may be pins, rigid or semi-rigid materials, and/or other types of conductive elements suitable for establishing electrical contact between the VL 502 and steerable endoscope 506. In other examples, the conductive elements 523 may be pre-embedded or otherwise included in the cartridge top interface surface 556 in alignment with electrical interfaces of the VL and endoscope. When the endoscope proximal end 514 is fully inserted into the alignment guide 527, elements of the VL 502 and endoscope 506 electrical interfaces may be caused to contact the conductive elements 523.

In operation, when the endoscope proximal end 514 is fully inserted into the cartridge alignment guide 527, and the cartridge 504 connected to the VL 502, as described, motors or other actuators cause conductive elements 523 of the electrical interface and impingement rod sets 524A-B to extend from the VL 502 through the cartridge apertures 529. The conductive elements 523 make electrical contact with an electrical interface of the steerable endoscope 506, and the impingement rod sets 524A-B mechanically couple to steering elements located in the endoscope proximal end 514 to cause steering movements of the distal tip.

In some examples, the VL 502 and steerable endoscope 506 include a sensor system for detecting the presence or absence of the endoscope proximal end 514 within the cartridge 504. For example, a sensor system (such as a magnet located in the steerable endoscope 506 and a Hall effect sensor located in the VL 502) may be used to detect whether the endoscope proximal end 514 is fully inserted into the cartridge alignment guide 527.

The endoscope coupling approach described in example video laryngoscope system 500 may facilitate the cleaning and/or sterilization of the VL 502 following intubation. For example, the sealed cartridge apertures 529 and endoscope apertures may reduce contamination of the VL 502 by the steerable endoscope 506 following post-loading of a breathing tube. In addition, the VL 502 may require few, if any, alignment features (such as edges, notches, etc.) for coupling the cartridge 504, which may reduce trapping of bio-contaminants, dirt, pathogens, etc., and may facilitate cleaning/wiping of the VL 502. The slim design of the cartridge 504 further enables one-time use or disposability of the cartridge 504 and/or steerable endoscope 506.

Figure 6:
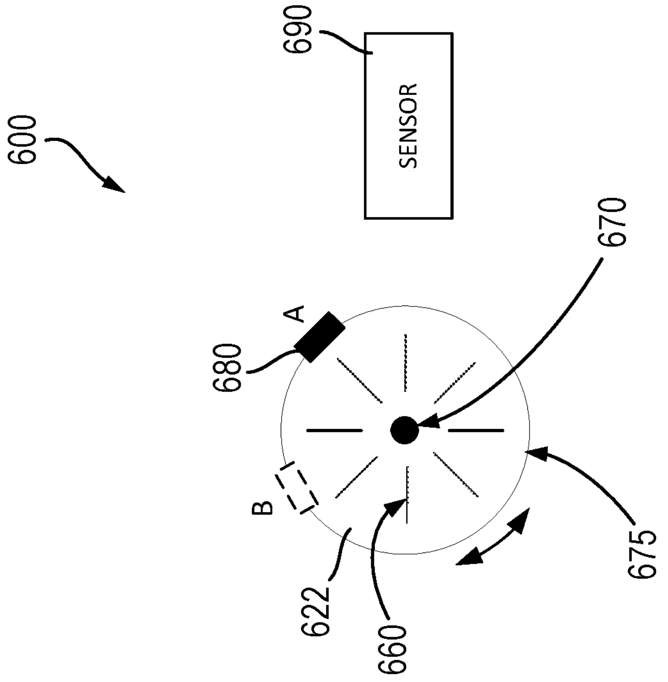
FIG. 6 depicts an example sensor configuration for determining endoscope distal tip orientation.

FIG. 6 depicts an example drum sensing system 600 for determining the orientation of an endoscope drum 622. When the distal end of the steerable endoscope is positioned in a patient's airway, the proximal end of the endoscope may be removed from the cartridge in order to post-load a breathing tube over the steerable endoscope, complete the intubation, or for another purpose. This manipulation of the endoscope proximal end may cause movement of the distal end of the endoscope within the patient, including movement of one or more drums connected to the pull wires. When the endoscope is reconnected to the VL, previously stored position data may no longer be accurate based on the movement of the pull wires or drums. To help alleviate this issue, sensors may be used to determine the positions of the drums, and thus the orientation of the steerable tip, when the endoscope is re-connected to the VL. For example, one or more sensors may be configured to determine the orientation, changes in orientation, and/or other positional parameters of the drum.

An example drum 622 is depicted in FIG. 6 from the viewpoint of a hub, axle, or other cartridge output drive (e.g., hub 425A or hub 425B) that engages the drum 622 when the cartridge and steerable endoscope are connected. The drum 622 includes engagement features 660 and a drum axis 670, around which the drum 622 rotates. In examples, drum 622 may include a drum magnet 680 (e.g., a permanent magnet) mounted to, or embedded within, a drum perimeter or outer surface 675. In other examples, the drum magnet 680 may be located on the interior of the drum 622, or may be located elsewhere on, within, or about drum 622. For instance, the drum magnet 680 may be located substantially near or at the center of rotation of the drum 622, such as with (or as part of) the drum axis 670. Further, the shape, N-S orientation, and mounting configuration of the drum magnet 680 may be selected to increase magnetic field sensing by the sensor 690. In some examples, a drum magnet 680 may be included with one or both drums 622 of the steerable endoscope, such as in drums 122A-B, 222A-B, etc., depicted in preceding drawings.

Sensor 690 may be a type of sensor capable of detecting magnetic fields, such as a Hall effect sensor, giant magnetoresistance (GMR) sensor, or other type of sensor. In some examples, the sensor 690 may be capable of detecting magnetic fields oriented along a single axis or along multiple axes (e.g., the sensor 690 may be a single- or multi-axis Hall effect sensor). The sensor 690 may be positioned in the cartridge or VL in a location suitable for detecting the magnetic field generated by the drum magnet 680, when the drum 622 is brought in proximity to the sensor 690. Although FIG. 6 depicts the sensor 690 as being located laterally from drum 622, the sensor 690 may be located, positioned, and/or oriented in the cartridge or VL as necessary to provide suitable detection and/or measurement of the magnetic field produced by drum magnet 680. For example, the sensor 690 may be placed substantially above or beneath, and centered on, the drum axis 670, to increase the sensitivity of the sensor 690 to rotations of the drum 622.

Detection of the drum magnet 680 by the sensor 690 allows for the rotational position of the drum to be determined. For example, the sensor 690 may be capable of detecting the presence and position of drum magnet 680 when the endoscope proximal end is fully inserted into the cartridge and/or when the cartridge is attached the VL.

In one example, the endoscope proximal end may be coupled into the detachable cartridge, with drum 622 initially oriented with drum magnet 680 in position A. The endoscope may be subsequently disconnected/detached from the detachable cartridge, such as during post-loading of a breathing tube, then re-inserted into the detachable cartridge. The process of removing and handling the endoscope proximal end may cause inadvertent rotation of the drum 622, which may result in drum magnet 680 moving to position B. When the endoscope proximal end is re-inserted into the detachable cartridge, the sensor 690 may detect the drum magnet 680 in position B. For example, the sensor may detect the change in position as a change in the magnitude and/or direction of the sensed magnetic field(s), which may correspond to the drum magnet in position B. That now known position B may be used for steering inputs of the VL.

In other examples, other types of sensing modalities may be used to detect inadvertent changes in orientation of one or both drums. For example, optical sensing methods may be used, where sensor 690 may include a light source and light detection elements. The drum outer surface 675 may include features that reflect light from the light source to the light detection element, such as angled surfaces, reflective coatings, and/or other reflective elements. In some examples the light source and light detection elements may be co-located in a common sensor package, while in other examples the light source and light detection elements may be arranged in separate locations around the drum 622 (such as may be required for light transmission, reflection, and/or detection). Further, one or both of the light source and light detection elements may be located in the cartridge and/or the VL. Light transmitted from the light source may be visible, infrared (IR), or other wavelength of light. The light source may include elements such as an LED, laser, or other type of light source. In some examples, light from the light source may be propagated toward one or more of the drums 622 through an optical window, optical fiber, light pipe, or other light transmission medium. Materials of the VL, detachable cartridge, and/or steerable endoscope may be optically transparent to support light transmission, detection, and/or other aspects of optical sensing. The light detection element may include photodiodes, phototransistors, or other type light detection element.

The sensor 690 may be associated with elements of the VL and/or detachable cartridge, such as one or more processors or similar components, that may receive and process the drum position/orientation data from sensor 690. If the received data indicates a shift in the position/orientation of drum 622, elements of the VL and/or cartridge may reconfigure, re-calibrate, and/or make other steering control adjustments. In one example, location A may represent an initial position of the drum magnet 680/drum 622, and by extension, location A may represent an initial position of the endoscope steerable tip. Location B may represent the maximum allowable rotation of the drum magnet 680/drum 622 in one direction (e.g., maximum anti-clockwise rotation), and by extension, may represent the maximum allowable bend angle of the endoscope steerable tip in one direction (e.g., maximum "left" bend). Elements of the VL and/or cartridge may reconfigure steering control input accordingly, to reflect that the endoscope steerable tip is at maximum "left" deflection. Elements of the VL may further provide a visual indication (such as on the VL display) of the change in endoscope steerable tip orientation based on received data from sensor 690.

Figure 7A:
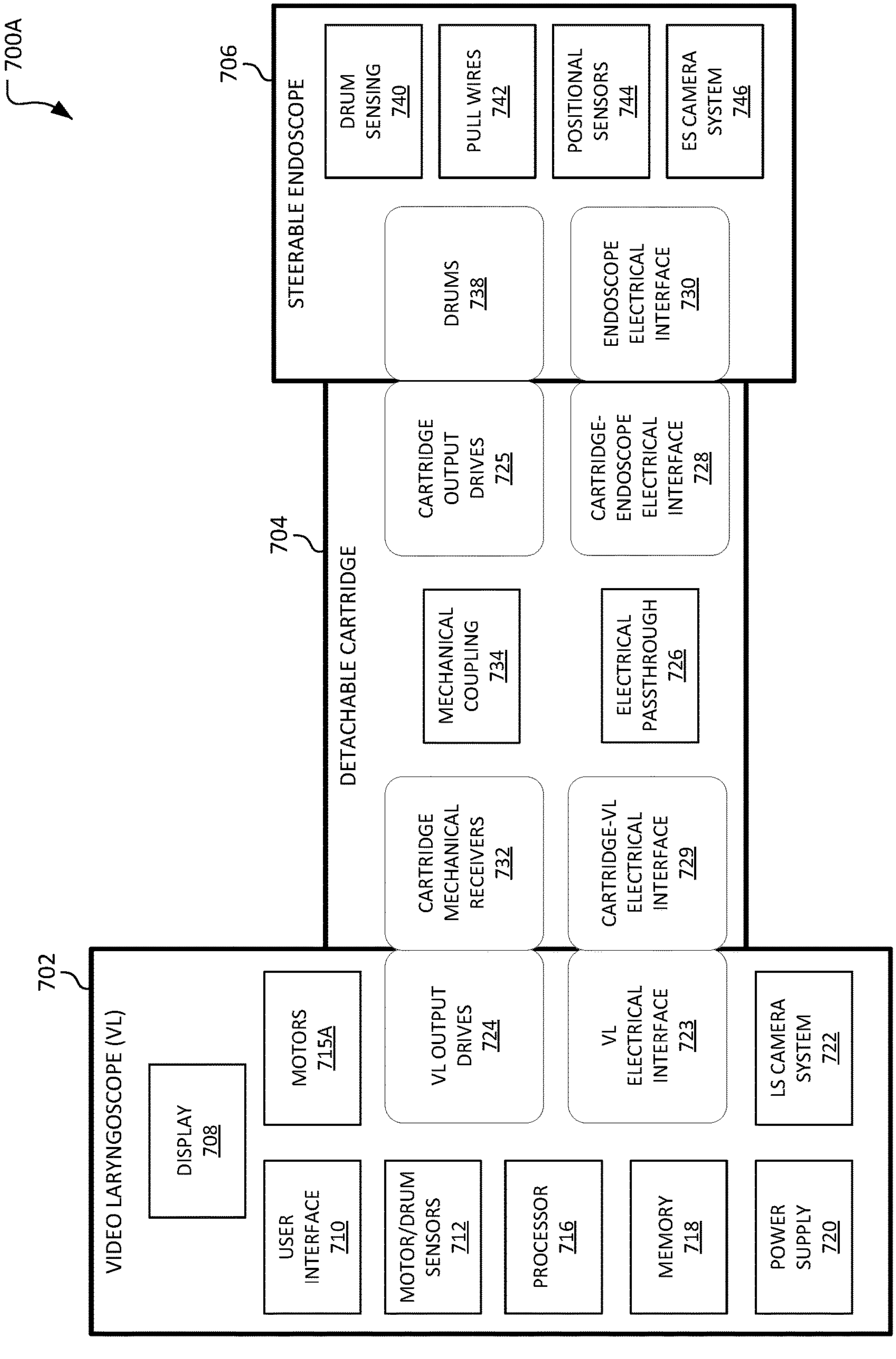
FIGS. 7A-7D are block diagrams of example combinations of a laryngoscope and an endoscope.

FIG. 7A-D are block diagrams of example configurations of video laryngoscope systems coupled to steerable endoscopes. FIG. 7A is a block diagram of an example system 700A in which the mechanical steering forces used to control the endoscope steerable tip are generated in the VL 702 and mechanically transmitted to the steerable endoscope 706 through the cartridge 704. Aspects of example system 700A may be similar to, or the same as, aspects of example systems above (e.g., system 200 of FIG. 2) in which an endoscope steerable tip is controllable via one or more electric motors included in the VL.

Referring now to FIG. 7A, the proximal end of the endoscope 706 may include elements of a mechanical interface for receiving the transmitted steering forces, and proximal end may include an electrical interface for receiving electrical power and transmitting/receiving communication signals.

The endoscope steerable tip may be controlled, in some examples, via pull wires 742 connected to an endoscope drive system including one or more drums 738. For instance, the pull wires 742 may connect to opposite sides of a rotatable element located in the endoscope proximal end, such as one of the drums 738 (which may be in the form of a capstan). The drums 738 may include force-receiving features that facilitate engagement of elements of cartridge output drives 725. In some examples, the pull wires 742 may connect to another type of mechanical element (such as a non-rotatable element), which may allow control of the endoscope steerable tip along one or more sets of movement axes.

The endoscope 706 may further include elements that are used for drum sensing subsystem 740. For example, elements used in drum sensing subsystem 740 may include magnets, optical elements or features, or other sensing elements that may be used to determine orientation of one or more drums 738. The endoscope steerable tip may include one or more positional sensors 744 and/or an endoscope camera system 746, which allows for video capture of the airway through the accessory interface of the endoscope steerable tip.

Endoscope 706 further includes an endoscope electrical interface 730 through which electrical power is provided to elements of the endoscope 706 (such as the endoscope camera system 746, positional sensors 744, etc.). The endoscope electrical interface 730 also enables elements of the endoscope 706 to transmit/receive communications signals to/from the cartridge 704 and/or VL 702. For example, the endoscope camera system 746 may receive electrical power from the endoscope electrical interface 730, transmit video data to the VL 702, and receive configuration information (such as preferred sample rate, video resolution, etc.) from the VL 702 via the endoscope electrical interface 730. As another example, positional sensors 744 may transmit steerable tip position/orientation data to the VL 702 and/or cartridge 704 via the endoscope electrical interface 730. The cartridge-endoscope electrical interface 728 may include a plurality of conductive elements similar and/or complimentary to the conductive elements of the endoscope electrical interface 730.

The cartridge 704 includes a cartridge-VL electrical interface 729 that electrically connects to a VL electrical interface 723 when the cartridge 704 is connected to the VL 702. In some examples, elements of the cartridge-VL electrical interface 729 may be similar to, or the same as, elements of cartridge-endoscope electrical interface 728. The cartridge-VL and cartridge-endoscope electrical interfaces 729/728 are connected within the cartridge 704 by way of the electrical passthrough 726.

In examples, the cartridge-VL electrical interface 729, electrical passthrough 726, and/or cartridge-endoscope electrical interface 728 may include passive or active components such as those discussed herein. In some examples, the cartridge 704 may include additional electronic components (e.g., sensors or other components) that connect to the cartridge-VL electrical interface 729, electrical passthrough 726, and/or cartridge-endoscope electrical interface 728, and receive electrical power and/or transmit/receive signals to elements of the VL 702 and steerable endoscope 706.

The cartridge 704 further includes cartridge output drives 725, which includes elements that engage and transmit steering forces to the endoscope drums 738. In examples, the cartridge output drives 725 may include hubs, axles, gears, rods, spindles, sprockets, couplings, linkages, and/or other elements designed to transmit steering forces to the drums 738. In some instances, the cartridge output drives 725 may include one set of the above elements for each of the drums 738 of the steerable endoscope 706. As an example, FIG. 4B depicts an example system 400 in which the cartridge 404 includes a hub 425A and B, and gear 428A and B for each of the endoscope drums 422A and B, respectively.

In addition, elements of the cartridge output drives 725 may include force-transmitting features that engage the drums 738, and elements of the cartridge output drives 725 and/or drums 738 may further include alignment features that automatically align the output drives 725 and the drums 738 when coupled. As an example, a hub of the cartridge output drives 725 may include a chamfer that facilitates alignment with one of the drums 738, when the steerable endoscope 706 is caused to connect to the cartridge 704. The hub may further include one or more guides that, when made to contact one of the drums 738 during coupling, cause small rotation of one of the drums 738, such that force-transmitting surfaces of the hub align with and engage opposing force-receiving surfaces of the drum. Similar features may be included in elements of the cartridge mechanical receivers 732 and/or VL output drives 724 to cause alignment and engagement between similar elements.

The cartridge mechanical receivers 732 may include drums, axles, and/or other elements capable of detachably engaging elements of the VL output drives 724. In some examples, the cartridge mechanical receivers 732 may include one set of the above elements for each drum 738 of the steerable endoscope 706. The cartridge mechanical receivers 732 may include features that facilitate engagement of elements of VL output drives 724.

The cartridge 704 may include a mechanical coupling 734 which transmits steering forces from the cartridge mechanical receivers 732, through the cartridge 704, to the cartridge output drives 725. The mechanical coupling 734 may include gears, axles, linkages, and/or other mechanical elements suitable for transmitting steering forces between elements of the cartridge mechanical receivers 732 and cartridge output drives 725. When the cartridge 704 is connected to the VL 702, steering forces generated by motors 715A are transmitted to the cartridge mechanical receivers 732 via the VL output drives 724.

One or more elements of the VL output drives 724 directly connect to the motors 715A, which may be a type of DC motor, such as stepper motors, servo motors, or other types of motors capable of generating sufficient force, torque, speed, and/or other motor performance parameters for causing movement of the endoscope steerable tip. The motors 715A may include analog and/or digital circuitry associated with providing electrical power and/or control of the motors 715A. In some examples, the motors 715A may include a single motor for each of the drums 738 of the steerable endoscope 706, while in other examples the motors 715A may include two or more motors for each of the drums 738. In examples where a single drum of the drums 738 controls movement of the endoscope steerable tip in two directions, a single motor of the motors 715A may control movement of the endoscope steerable tip.

Elements of the VL output drives 724 may rotate in response to rotational force applied by the motors 715A, and when the VL output drives 724 are coupled to elements of the cartridge mechanical receivers 732, the VL output drives 724 may cause rotation of the elements of the cartridge mechanical receivers 732. In other examples, elements of the VL output drives 724 may translate output rotational forces produced by the motors 715A into linear, oscillatory, non-uniform, or other type of motion, which may then be coupled to elements of the cartridge mechanical receivers 732. These non-rotational forces may be further transmitted through the cartridge 704 to the endoscope 706 or may be translated back to rotational forces within the cartridge 704 or endoscope 706.

Motor/drum sensors 712 may observe and measure aspects of the functioning of the motors 715A. For example, the motor/drum sensors 712 may measure motor axle position, axle rotational speed, power consumption, current consumption, and/or other metric of motor functionality. In examples, the motor/drum sensors 712 may be associated with servo control of motors 715A or another feedback control method. In some instances, the motor/drum sensors 712 may measure motor 715A functionality indirectly, such as by measuring or sensing the motion of gears, axles, and/or other elements associated with input to, or output from, the motors 715A. The motor/drum sensors 712 may include capacitive, inductive, resistive, optical, and/or other types of sensing elements, components, and/or devices suitable for measuring functional performance of the motors 715A. The motor/drum sensors 712 may further include analog or digital circuitry associated with the processing of signals generated by sensing activity.

In other examples, the motor/drum sensors 712 may include portions of a sensor system used to determine orientation of the endoscope drums 738. For instance, motors/drum sensors 712 may include elements described above relating to sensor 690 depicted in FIG. 6. In some examples, sensors or other elements associated with functions of the drum sensing subsystem 740 may be included in the cartridge 704.

Elements of the VL 702 (e.g., processor 716, described below) may use sensor data acquired by motor/drum sensors 712 and drum sensing subsystem 740 (if applicable) to determine orientation of one or more endoscope drums 738, and by extension, orientation of the endoscope steerable tip. The VL may reconfigure steering control accordingly, so that dynamic range of steering control correlates with the actual dynamic range of steerable tip movement. This process was described in detail in relation to FIG. 6 above.

In addition to elements associated with motor output and mechanical coupling to the cartridge 704, the VL 702 includes a VL electrical interface 723 that electrically couples the VL 702 to the cartridge 704. When the VL 702, cartridge 704, and endoscope 706 are coupled, electrical connection is established between the VL electrical interface 723, cartridge-VL electrical interface 729, electrical pass-through 726, cartridge-endoscope electrical interface 728, and/or endoscope electrical interface 730. Thus, electrical communication between the VL 702, cartridge 704, and the endoscope 706 is enabled. In examples where the steerable endoscope 706 has been decoupled from the cartridge 704 (such as during post-loading of a breathing tube), the cartridge 704 may remain electrically connected to the VL 702, and may receive power from, and communicate with, the VL 702.

The VL electrical interface 723 may include passive or active components associated with electrical signal communication and with the provision of electrical power to elements of the endoscope 706 and/or cartridge 704. In some examples, the VL electrical interface 723 may be associated with receiving sensor data from positional sensors 744, drum sensing subsystem 740 (if applicable), and/or other sensors of the steerable endoscope 706. The VL electrical interface 723 also receives video image data from ES camera system 746 and may include elements that direct the video images to be displayed on display 708.

The VL 702 also includes a processor 716, which may include one or more general purpose processors, microprocessors, microcontrollers, graphics processing unit (GPU), digital signal processors (DSPs), or other programmable circuits. In examples, the processor 716 may include any combination of commercially available components, and/or custom or semi-custom integrated circuits, such as application specific integrated circuits (ASICs). The processor 716 may include elements needed for control or communication with the display 708, user interface 710, motor/drum sensors 712, motors 715A, memory 718, power supply 720, VL camera system 722, and/or VL electrical interface 723. The processor 716 may perform control, interface, communication, or other processing functions by executing instructions that are stored in the memory 718. For instance, the memory 718 may store instructions that, when executed by the processor 716, cause the elements of the system 700A to perform operations described herein. The memory 718 may include RAM, ROM, electrically erasable programmable read-only memory (EEPROM), flash memory or other memory technology.

Further, the processor 716 and/or elements of the VL electrical interface 723 may direct or manage functions associated with electrical communication between the VL 702, cartridge 704, and/or steerable endoscope 706. In examples, the processor 716 may be associated with the processing and display of video images received from the ES camera system 746 through the VL electrical interface 723. The processor 716 may also be associated with the reception and processing of sensor data, such as data produced and received from motor/drum sensors 712, drum sensing subsystem 740, positional sensors 744, and/or other source of sensor data.

In some examples, the processor 716 and/or elements of the VL electrical interface 723 may manage or participate in a signal communications interface or protocol for transmitting and receiving data. For example, data may be transmitted/received between the VL 702, cartridge 704, and steerable endoscope 706 via serial peripheral interface (SPI), inter-integrated circuit (I2C), and/or other type of data transfer interface or protocol. Elements of the processor 716 and/or VL electrical interface 723 may provide or receive support signaling for data transmission/reception, such as clock(s), timing, enable, and/or other types of signals required for data transmission/reception.

The VL 702 also includes an VL camera system 722. In examples, the VL camera system 722 may include one or more video cameras and light sources, optical transmission media, video processing components, and/or other components associated with video image capture of the airway. The VL camera system 722 may be distributed within the VL 702, such as in the blade or extension (such as extension 210 or 310), handle (such as handle 208 or 308), compartment of the VL 702 (such as drive housing 220), or portions of the display 708 (such as display 212, 312, 512, etc.). In some examples, elements of the VL camera system 722 may be integrated into other features of the VL 702, such as in a dedicated camera mount associated with the blade or other aspect of the VL 702. For example, elements of the VL camera system 722 may be integrated into a type of camera mount referred to in some examples as a "camera stick" that couples to the laryngoscope blade.

Video images captured by the VL camera system 722 may be directed by the VL camera system 722 or by the processor 716 (or other element of VL 702) to be displayed on display 708. For instance, the display 708 may be capable of simultaneous display of video images from the VL camera system 722 and from endoscope camera 746, or the display 708 may be capable of switching between either source of video images.

The display 708 may further be used to display status, data, or other types of information associated with the operation of VL 702, cartridge 704, and/or steerable endoscope 706. For example, the display 708 may indicate presence/absence of the cartridge 704 and/or steerable endoscope 706. The display 708 may also indicate poor connection between the VL 702, cartridge 704, and/or steerable endoscope 706. In other examples, the display 708 may display sensor data (such as orientation of the endoscope steerable tip), motor output data, fault conditions, steering-related data, and/or any other indications associated with status, function, and/or operation of example system 700A.

The display 708 may be a touch-sensitive display (e.g., a capacitive touch-sensitive display) that allows user input to be received through the display 708. A touch-sensitive display 708 may provide an interface for receiving user control inputs to the endoscope steerable tip and/or for user configuration of example system 700A. In some examples, a graphical user interface (GUI) may be provided on the display 708 by a user interface 710 for receiving user input. The GUI may include soft menus or similar features that allow a user to configure settings, enable features or functions, set operating parameters, store data (such as user-specific data), and/or modify other user-configurable inputs.

The user interface 710 may also receive input from other types of components, such as buttons, switches, knobs, and/or other input components associated with the VL 702. In some examples, the user interface 710 may receive input from an external controller (not depicted) for steering the tip of the steerable endoscope 706. For instance, an external directional controller may operatively couple to the VL 702 and provide steering control input to the endoscope steerable tip, through elements associated with the user interface 710, and/or with other elements, components, or systems of VL 702.

In examples where the display 708 provides for steering control of the endoscope steerable tip (such as when the display 708 is a touch-sensitive display), the user interface 710 may include a steering feature as part of the above-described GUI. Input steering control may be received through the GUI by the user interface 710 and translated by the user interface 710, processor 716, and/or elements of the motors 715A into corresponding control input to the motors 715A.

The VL 702 includes a power supply 720, such as a battery, which may be housed in a suitable compartment of the VL. For example, a battery may be contained in the handle of the VL 702. The power supply 720 may further include analog or digital circuitry associated with control, regulation, and/or distribution of electrical power to elements of the VL 702, cartridge 704, and/or steerable endoscope 706.

Figure 7B:
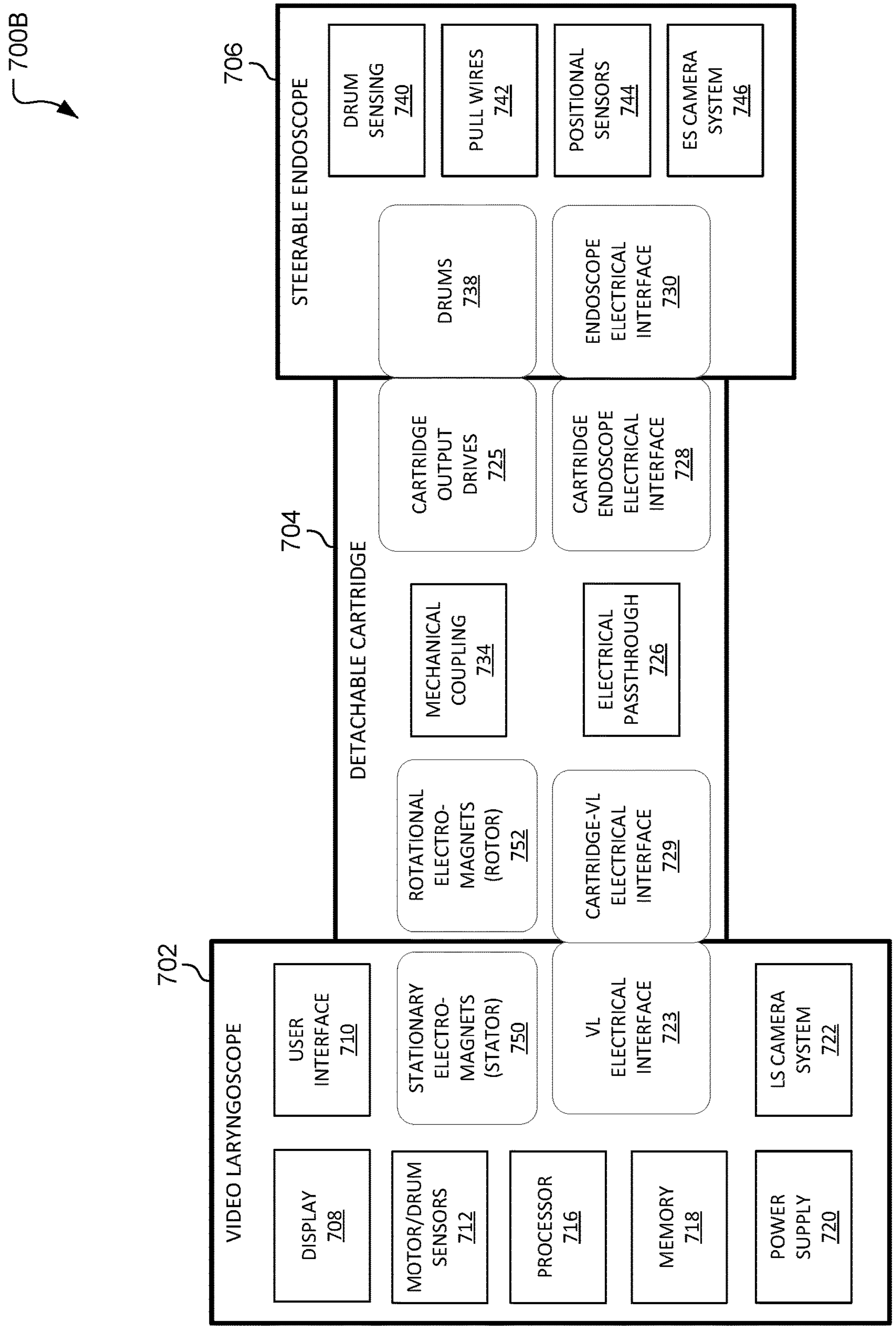

FIG. 7B is a block diagram of an example system 700B in which the steering forces used to control the endoscope steerable tip are generated by stationary electromagnetic elements in the VL 702, and inductively coupled to rotational electromagnetic elements in the cartridge 704. Aspects of example system 700B may be similar to, or the same as, aspects of example systems 300 and 400 (of FIGS. 3 and 4B, respectively), in which an endoscope steerable tip was controllable via one or more axial motors split between the VL and detachable cartridges of those example systems. Additional details of such an example were provided above for FIGS. 3, 4A, and 4B.

Referring now to FIG. 7B, the stationary electromagnets 750 of VL 702 may include one or more electromagnets, each formed from coiled or wound conductors (e.g., coils). The stationary electromagnets 750 may be formed from flexible or rigid wire, or any other form of conductive material suitable for forming an electromagnetic coil. The stationary electromagnets 750 may be wound in any of a wide variety of shapes and configurations, such as substantially flat, circular coils, and may be spatially arranged to produce a specific output magnetic field directivity. Selection and/or design of the stationary electromagnetics 750 may include specifying the location, position, orientation, conductor material, conductor diameter or cross-section, number of coils, number of windings in each coil, finished coil dimensions, and/or other factors typically considered during inductive circuit design. In some examples, the electromagnetic coils of stationary electromagnets 750 may include one or more core elements, which may have specified levels of ferromagnetic properties for control of magnetic flux. In other examples, the electromagnetic coils may have an air core.

Stationary electromagnets 750 of the VL 702 may further include any passive circuit components, active circuit components, analog circuitry, and/or digital circuitry associated with the conduction of current through electromagnetic coils of the stationary electromagnets 750. For example, the stationary electromagnets 750 may include current sources, voltage sources, voltage regulators, switching elements, sensors, semiconductor devices (such as diodes, transistors, etc.), passive components (e.g., capacitors, inductors, resistors), and/or other circuit components associated with the conduction of current through elements of the stationary electromagnets 750.

The rotational electromagnets 752 of the VL 702 may include one or more wound electromagnetic coils, permanent magnets, and/or other electromagnetic elements that are spatially arranged and affixed to a common structure. For instance, elements of the rotational electromagnets 752 may be mounted in a circular arrangement to a disc, frame, or other structure capable of rotating around a central axis when suitable force is applied to the elements of the rotational electromagnets 752. Further, elements of the rotational electromagnets 752 may be arranged to inductively couple magnetic fields produced by the stationary electromagnets 750, which may exert force on the rotational electromagnets 752 and cause rotation. In examples, the stationary electromagnets 750 and rotational electromagnets 752 may be arranged to form the stator and rotor (respectively) of an axial motor. This arrangement was depicted and described in detail in FIGS. 3 and 4. In some examples, a single stator and rotor (i.e., a single axial motor) may be coupled to one of the drums 738 (directly or indirectly), allowing a single axial motor to control the endoscope steerable tip along a single set of one or more movement axes.

Within the cartridge 704, the rotational electromagnets 752 are connected to elements of the mechanical coupling 734. Magnetic fields coupled to the rotational electromagnets 752 impart force on the rotational electromagnets 752, which in turn transmit the imparted force to the mechanical coupling 734. As described for FIG. 7A, the mechanical coupling 734 is connected to the cartridge output drives 725, which is further connected to drums 738 when the cartridge 704 and steerable endoscope 706 are coupled. Magnetic fields produced by the stationary electromagnets 750 may therefore transmit steering forces from the VL 702 to the cartridge 704, which translates the coupled forces to mechanical control of the endoscope steerable tip.

While not depicted in FIG. 7B, in some examples, the cartridge 704 may include sensors associated with the rotational electromagnets 752. The sensors may provide data related to the operation of the rotational electromagnets 752, such as position/orientation, rotational speed, and/or other metrics of motor functionality. Additionally or alternatively, the cartridge 704 may include sensors associated with the mechanical coupling 734 and/or cartridge output drives 725.

VL 702 includes motor/drum sensors 712, which may include sensors associated with the stationary electromagnets 750. The sensors may measure current consumption, power consumption, temperature, and/or other metrics related to operational performance of the stationary electromagnets 750. Motor/drum sensors 712 may further include sensors associated with determining orientation of drums 738, which was described in relation to FIGS. 6 and 7A.

In example system 700B, the user may provide steering control input through the display 708 (which may be a touch-sensitive display) or through an external directional controller as described for FIG. 7A. Elements of the display 708, user interface 710, processor 716, and/or stationary electromagnets 750 may translate the received steering control inputs to corresponding control currents conducted through elements of stationary electromagnets 750, for exerting control of the endoscope steerable tip via magnetic field coupling. Remaining elements of the VL 702, cartridge 704, and steerable endoscope 706 (such as memory 718, electrical passthrough 726, positional sensors 744, etc.) may be substantially as described for FIG. 7A.

Figure 7C:
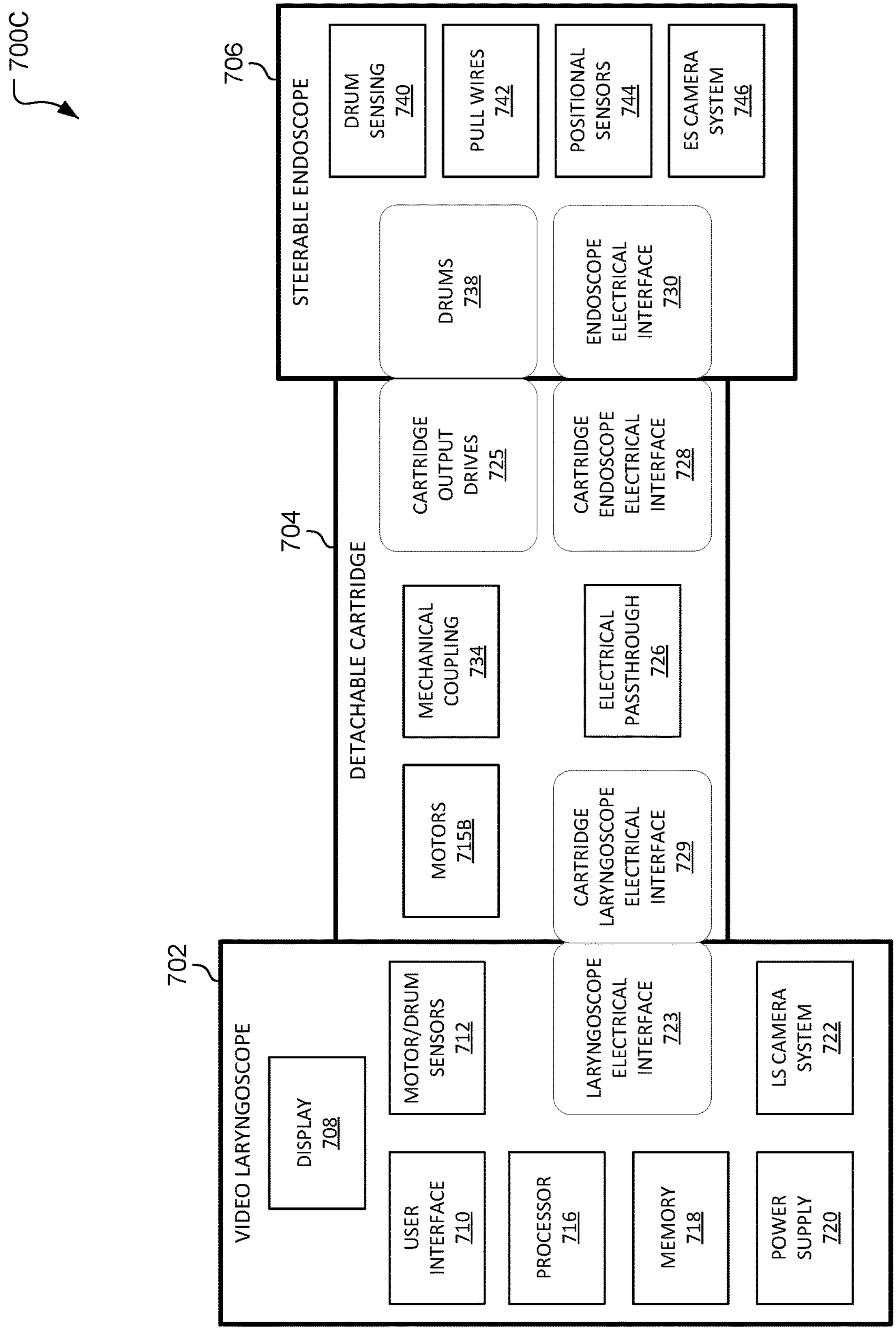

FIG. 7C is a block diagram of an example system 700C in which the steering forces used to control the endoscope steerable tip are generated by motors 715B included in the cartridge 704. The motors 715B may be a type of DC motor, such as servo motors, stepper motors, or other type of motors, and may include analog and/or digital circuitry associated with providing electrical power and/or control of the motors 715B. The rotational axle or other mechanical element of each of the motors 715B may be connected to (and transmit steering forces to) one or more elements of the mechanical coupling 734, such as gears, axles, and/or other elements of the mechanical coupling 734. As described for FIG. 7A, the mechanical coupling 734 is connected to the cartridge output drives 725, which are further connected to the drums 738 when the cartridge 704 and steerable endoscope 706 are coupled.

In some examples, the motors 715B may include a single motor for each of the drums 738 of the steerable endoscope 706, while in other examples the motors 715B may include two or more motors for each of the drums 738. Where a single motor of the motors 715B is used to control one of the drums 738, the mechanical coupling 734 and cartridge output drives 725 may include corresponding sets of elements sufficient for linking each of the motors 715B to each of the drums 738, accordingly.

While not depicted in FIG. 7C, in some examples, the cartridge 704 includes sensors associated with the motors 715B. The sensors may provide data related to the operation of the motors 715B, such as motor axle position/orientation, axle rotational speed, power consumption, current consumption, and/or other metrics of motor functionality. Additionally or alternatively, the cartridge 704 may include sensors associated with the mechanical coupling 734 and/or cartridge output drives 725, and may measure position, orientation, speed, state, or other measure associated with elements of mechanical coupling 734 and/or the cartridge output drives 725.

Data produced by sensors in the cartridge 704 may be received and/or processed by elements of the VL 702, such as the motor/drum sensors 712, processor 716, and/or other elements of the VL 702. Motor/drum sensors 712 may further include sensors associated with determining orientation of drums 738, which was described in relation to FIGS. 6 and 7A.

In example system 700C, the user may provide steering control input through the display 708 (which may be a touch-sensitive display) or through an external directional controller as described for FIG. 7A. Elements of the display 708, user interface 710, and/or processor 716 may translate the received steering control inputs to corresponding control signals for controlling the motors 715B. These control signals may be transmitted to the motors 715B via the VL electrical interface 723 and cartridge-VL electrical interface 729. The VL electrical interface 723 may also be used to provide electrical power to the motors 715B.

Remaining elements of the VL 702, cartridge 704, and steerable endoscope 706 (such as memory 718, electrical passthrough 726, positional sensors 744, etc.) may be substantially as described for FIG. 7A.

Figure 7D:
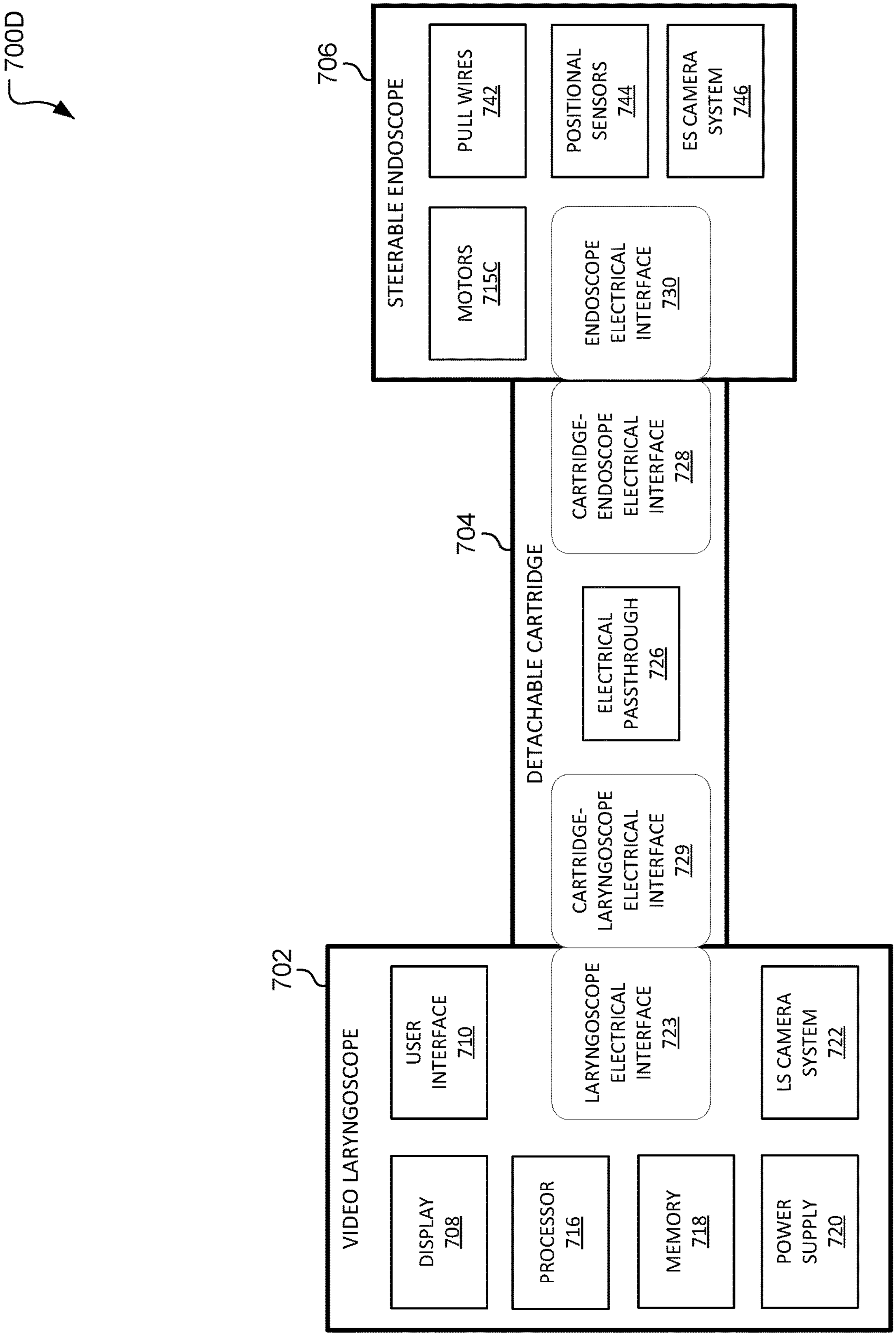

FIG. 7D is a block diagram of an example system 700D in which the steering forces used to control the endoscope steerable tip are generated by motors 715C included within the steerable endoscope 706. The motors 715C may be a type of DC motor, such as servo motors, stepper motors, or other type of motors, and may include analog and/or digital circuitry associated with providing electrical power and/or control of the motors 715C. The motors 715C may include elements that couple to pull wires 742 or other elements used to control the steerable tip.

The VL 702 provides electrical power and motor control to the motors 715C via the VL electrical interface 723, which is electrically connected to endoscope electrical interface 730 through electrical interface elements of the cartridge 704. As depicted in example system 700D, the cartridge 704 may substantially serve as an electrical passthrough, when the VL 702, cartridge 704, and steerable endoscope 706 are coupled.

In example system 700D, the user may provide steering control input through the display 708 (which may be a touch-sensitive display) or through an external directional controller as described for FIG. 7A. Elements of the display 708, user interface 710, and/or processor 716 may translate the received steering control inputs to corresponding control signals for controlling the motors 715C. These control signals may be transmitted to the motors 715C via the VL electrical interface 723 and the electrical interfaces of the cartridge 704 and steerable endoscope 706.

Remaining elements of the VL 702, cartridge 704, and steerable endoscope 706 (such as memory 718, electrical passthrough 726, positional sensors 744, etc.) may be substantially as described for FIG. 7A.

Figure 8:
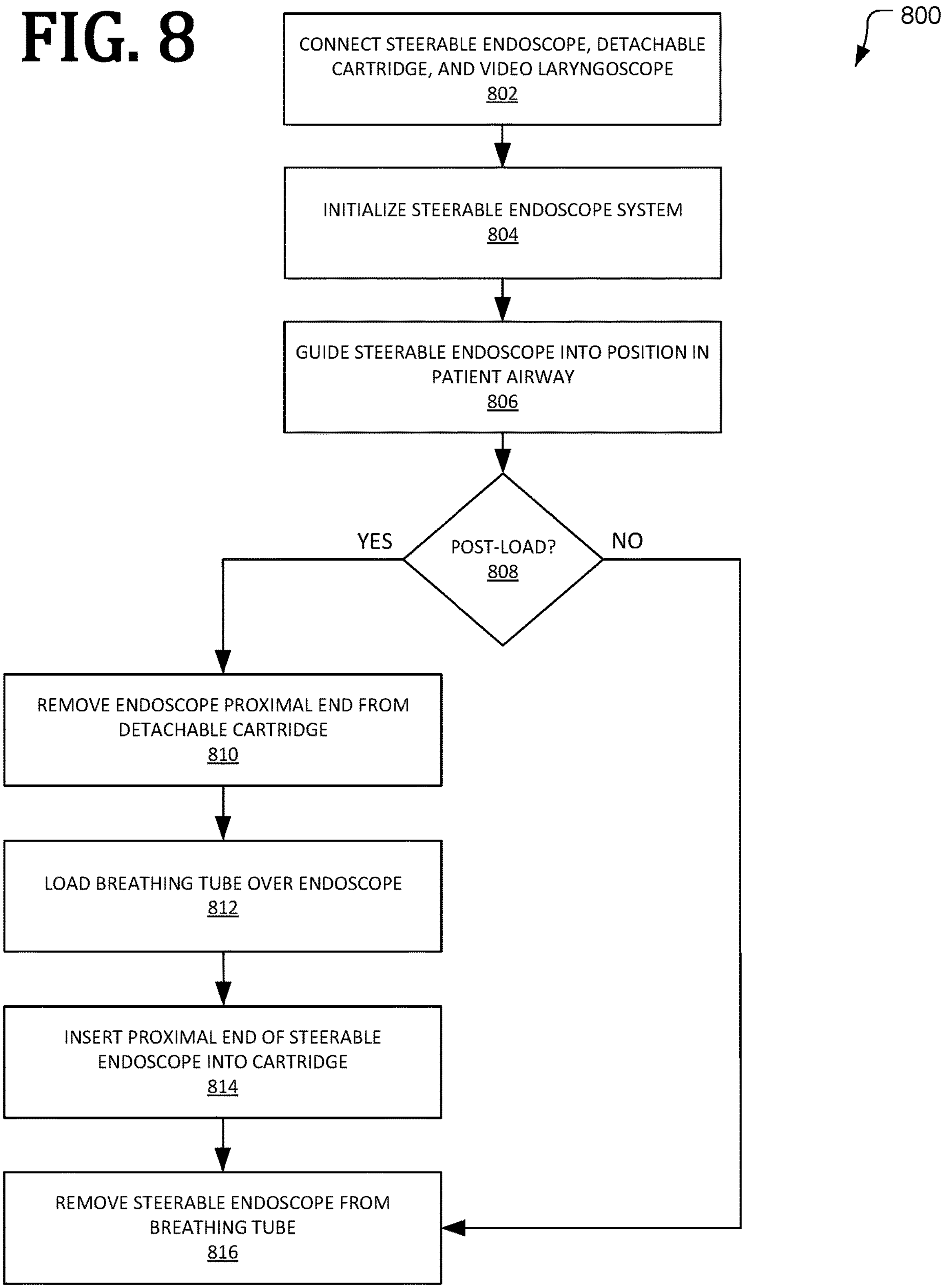
FIG. 8 depicts an example method for performing an intubation using the video laryngoscope and endoscope systems described herein.

FIG. 8 depicts an example method 800 for performing an intubation using a laryngoscope/endoscope combination. At operation 802, the steerable endoscope, detachable cartridge, and VL are connected. The steerable endoscope (such as steerable endoscope 106, 206, 306, 406, 506, 706) may be connected to the cartridge (such as 104, 204, 304, 404, 504, 704) by one of several possible methods. For example, the proximal end of the steerable endoscope may be fully inserted into the detachable cartridge, such as through a dedicated endoscope port (such as endoscope port 207), retention guide (such as retention guide 327), alignment guide (such as alignment guide 527), or other element of the cartridge designed to receive the endoscope proximal end. In examples, the endoscope may slide, snap, or be connected to the cartridge via another method.

In some examples, the cartridge may provide a feature (such as a button, knob, etc.) that causes force to be applied to the endoscope proximal end. The applied force may retain the endoscope proximal end in the cartridge and may cause mechanical and/or electrical elements of the endoscope to become connected to, and engage, corresponding elements of the detachable cartridge.

The cartridge is further connected to the VL. As described above, retention magnets, spring-loaded elements, guides, notches, and/or other features or elements of the cartridge and/or VL may facilitate or cause alignment and retention of the cartridge to the VL. When the VL is connected to the detachable cartridge, mechanical and/or electrical elements of the VL and corresponding mechanical and/or electrical interface elements of the cartridge are connected.

In examples, the VL, detachable cartridge, and endoscope may be connected together in any order. In further examples, the cartridge may be connected to the VL with or without the steerable endoscope being connected to the detachable cartridge. In some examples, a breathing tube may be preloaded over the endoscope prior to connecting the endoscope to the detachable cartridge.

At operation 804, with the VL, detachable cartridge, and steerable endoscope connected, the VL may perform an initialization of the connected system, whereby the VL may apply power to, and establish communication with, electrical elements of the steerable endoscope (such as positional sensors 744, endoscope camera system 746, etc.) and cartridge (if applicable). In examples where the VL includes motors (such as motors 715A) for generating steering force for controlling the endoscope steerable tip, the VL may apply power to the motors and associated circuitry and establish communication between elements of the VL associated with control of the motors (such as processor 716, user interface 710, motors 715A, etc.). The VL may further initialize and display a GUI for receiving steering control input.

In examples where the cartridge is connected to the VL with no steerable endoscope present, the VL may initialize electrical elements of the detachable endoscope, if applicable. In other examples, the VL may perform initialization once the endoscope is connected to the detachable cartridge.

At operation 806, the steerable endoscope may be guided into the patient's airway. An endoscope camera system may provide video images of the airway that are displayed on the display of the VL (such as display 112, 212, 312, etc.) as the distal end of the endoscope is guided into position. Directional control of the steerable tip may be received from the display (if the display is a touch-sensitive display) or from an external directional controller that is operatively coupled to the VL. The steering control inputs are translated to appropriate control signals for one or more motors (DC, axial, etc.) or other actuator, which causes movement of the steerable tip, accordingly.

At operation 808, in examples where post-loading of a breathing tube over the steerable endoscope is unnecessary, flow proceeds "NO" to operation 816. One scenario in which it may be unnecessary to post-load a breathing tube is when the endoscope is used strictly to provide video imagery of the airway, such as to provide a supplemental view of the airway not achievable with a video camera of the VL. Another scenario in which it may be unnecessary to post-load a breathing tube is when the breathing tube is preloaded, prior to guiding the endoscope into the airway. At operation 816, once a clinician has completed the intubation, the steerable endoscope may be removed from the breathing tube (if applicable), by sliding the steerable endoscope out through the proximal end of the breathing tube.

At operation 808, in examples where a clinician prefers to post-load a breathing tube over the endoscope, flow proceeds "YES" to operation 810, where the endoscope proximal end may be removed from the detachable cartridge. In some examples, the cartridge may remain connected to the VL, while in other examples the cartridge may be removed from the VL. Removal of the endoscope proximal end from the cartridge may include releasing retention and/or coupling forces applied by the cartridge to the endoscope proximal end. For example, features of the cartridge (such as a button, knob, etc.) may be disengaged to release the retention and/or coupling forces applied to the endoscope proximal end.

At operation 812, a breathing tube may be loaded over the endoscope, such as by sliding the breathing tube over the endoscope proximal end and along the length of the steerable endoscope, until the distal end of the breathing tube is in a preferred position in the airway.

At operation 814, with the breathing tube positioned, the endoscope proximal end may, if necessary, be re-inserted into the cartridge as previously described. For instance, the clinician may optionally choose to re-insert the endoscope proximal end in order to confirm or adjust breathing tube placement, if needed. In some examples, prior to re-inserting the endoscope proximal end into the detachable cartridge, the endoscope proximal end, detachable cartridge, and/or VL may be sanitized or wiped to remove bio-contaminants and/or pathogens.

While the endoscope proximal end is removed from the cartridge for loading the breathing tube (or for some other purpose), handling of the endoscope may result in unintended disturbance of the endoscope mechanical interface (e.g., one or more drums). Disturbance of the endoscope mechanical interface may affect the steerable tip position, which may affect steering control of the tip. For example, the endoscope drums may be inadvertently rotated during handling, resulting in movement of the endoscope steerable tip away from the preferred position, and possibly towards the limit of allowable range of movement of the steerable tip. During re-insertion of the endoscope proximal end, the VL may determine the position of the steerable tip using sensors associated with the drums (such as drum sensing subsystem 740) and adjust or reconfigure the steering control accordingly. An example of this process was described in relation to FIGS. 6 and 7A above.

Figure 9:
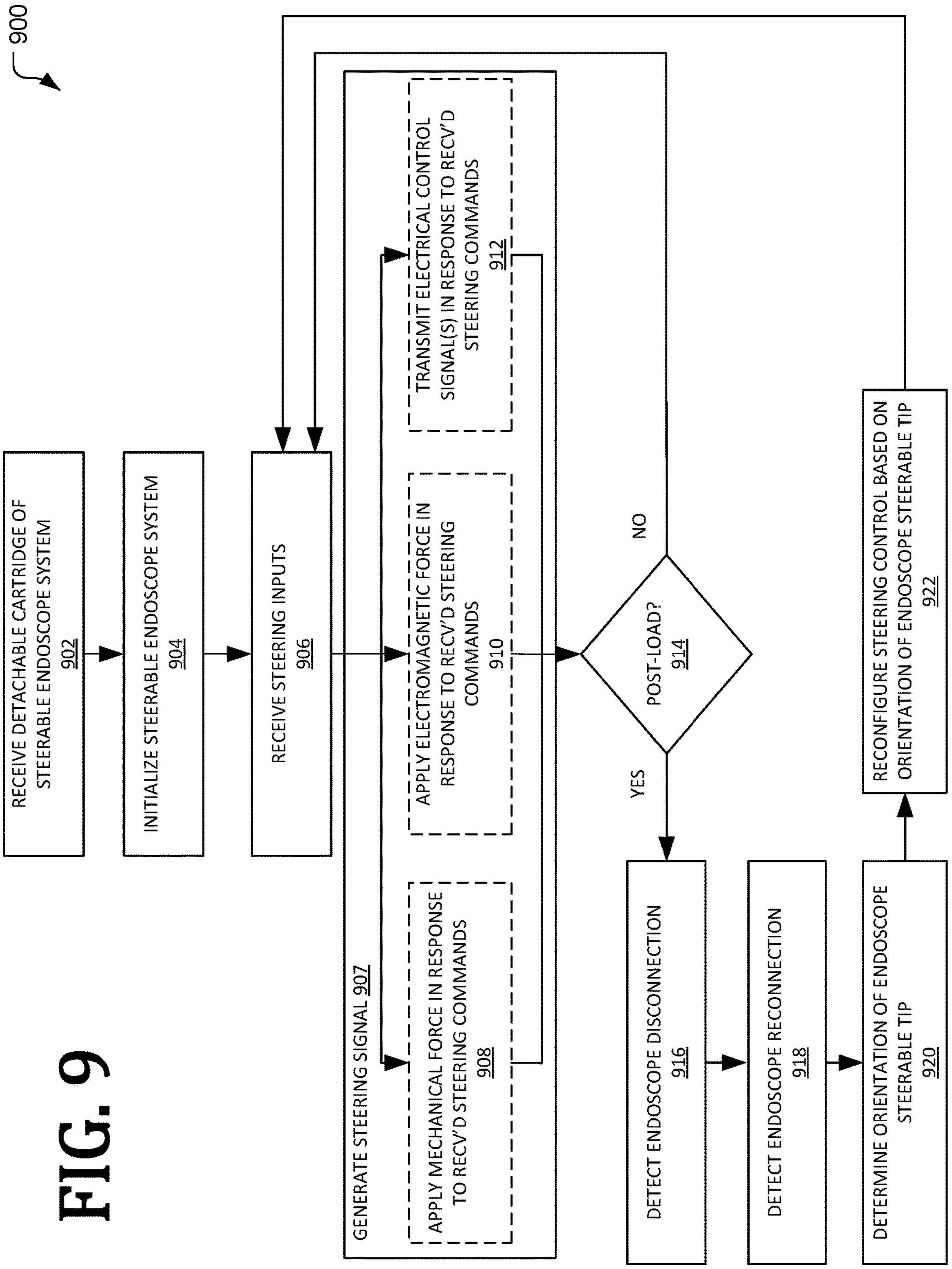
FIG. 9 depicts an example method for controlling an endoscope coupled to a laryngoscope.

FIG. 9 depicts an example method 900 for controlling a steerable endoscope coupled to a VL via a detachable cartridge. At operation 902, the VL receives the detachable cartridge. As described above, retention magnets, spring-loaded elements, guides, notches, and/or other features or elements of the cartridge and/or VL may facilitate or cause alignment and retention of the cartridge to the VL. When coupled, mechanical and/or electrical elements of the VL and corresponding mechanical and/or electrical elements of the cartridge are connected.

In examples, the VL, detachable cartridge, and steerable endoscope may be connected together in any order. In further examples, the cartridge may be connected to the VL with or without the steerable endoscope first being connected to the detachable cartridge. In some examples, a breathing tube may be pre-loaded over the endoscope, prior to connecting the endoscope to the detachable cartridge, while in other examples the breathing tube may be post-loaded once the endoscope has been guided into position in the patient's airway.

Operation 902 may also include detecting, by the VL, the connection of the cartridge to the VL. For instance, when an electrical connection is established between the VL and the cartridge, such a connection may be detected by the VL. In response, the VL may display an indication that the cartridge has been attached. For instance, an indicator icon may be displayed on the screen that indicates the cartridge has been connected and/or endoscope functionality is available.

At operation 904, the VL may perform an initialization of the connected system, whereby the VL may apply power to, and establish communication with, electrical elements of the steerable endoscope (such as positional sensors 744, endoscope camera system 746, etc.) and electrical elements of the cartridge (if applicable). In examples where the VL includes motors (such as motors 715A) for generating steering force for controlling the endoscope steerable tip, the VL may apply power to the motors and associated circuitry and establish communication between elements of the VL associated with control of the motors (such as processor 716, user interface 710, motors 715A, etc.). The VL may further initialize and display a GUI for receiving steering control input.

In examples where the cartridge is connected to the VL with no steerable endoscope present, the VL may initialize electrical elements of the detachable endoscope, if applicable. In other examples, the VL may perform initialization once the endoscope is connected to the detachable cartridge.

At operation 906, the VL receives steering input(s) for controlling the endoscope steerable tip. In one example, the VL may receive steering inputs from a touch-sensitive display of the VL (such as display 112). In other examples, the VL may receive steering inputs from an external directional controller that is operatively coupled to the VL. The VL may receive steering inputs while the steerable endoscope is guided into a patient's airway. In examples, the steering inputs may be at least partially based on video images received from a video camera mounted within the steerable endoscope and displayed on the display of the VL during the process of guiding the steerable endoscope into the patient's airway.

At operation 907, the VL generates a steering signal based on the steering input(s). The steering signal causes movement of the respective motors or components of the system depending on the particular configuration. For example, if a "left" input is received as the steering input, the VL generates a steering signal that causes a respective motor to rotate, which in turn causes a drum of the endoscope drive system to rotate and a pull wire to be pulled to cause the steerable tip to bend or articulate to the left. The steering signal may also indicate an amount that the steerable tip is to be moved, and the motor may rotate a corresponding amount. Accordingly, when a steering input is received, the VL may determine which motor is to be activated to cause the intended direction, the direction the motor is to turn (e.g., clockwise or counterclockwise), and the amount the motor should rotate (e.g., number of degrees) to achieve the desired steering of the distal tip of the endoscope.

As depicted in the figures discussed above, such as FIGS. 7A-7D, elements that provide control of the endoscope steerable tip may be arranged in a number of configurations and distributed amongst the VL, the cartridge, and the endoscope. Depending on the particular configuration of the system, one of operation 908, operation 910, or operation 912 is performed to translate the steering commands into a steering signal that causes physical movement of the steerable tip of the steerable endoscope.

In examples where steering forces are generated by motors included in the VL (and mechanically coupled to the steerable endoscope via the detachable cartridge), at operation 908, motors of the VL apply mechanical force in response to the received steering inputs. The received steering inputs may be translated by elements of the VL into corresponding signals for controlling motor output. For example, elements of the VL may translate steering inputs into corresponding electrical current applied to one or more of the motors. The current applied to one or more of the motors may correspond to output steering force(s) necessary to move the endoscope steerable tip in a particular direction (e.g., along one or more axes) and by a prescribed amount.

The steering force generated by one or more of the motors may be applied to a mechanical interface of the VL (such as VL output drives 724), which may further apply the steering force to a mechanical interface of the cartridge (such as cartridge mechanical receivers 732). The steering forces may then be transmitted by elements of the cartridge to mechanical elements of the steerable endoscope associated with control of the steerable tip.

In other examples (such as example system 500 of FIG. 5), motors or other actuators of the VL may apply steering forces directly to mechanical elements of the steerable endoscope associated with control of the endoscope steerable tip. For example, the VL may cause one or more impingement rod sets (such as impingement rod sets 524A-B) to extend through one or more sealed apertures in the cartridge (such as apertures 529) and directly engage mechanical steering elements of the endoscope.

Alternatively, in examples where steering forces are generated by electromagnetic elements in the VL (such as stationary electromagnets 750 or stators 432), at operation 910, electromagnets of the VL apply electromagnetic force in response to the received steering inputs. Elements of the VL may translate the received steering control inputs into corresponding electrical current applied to one or more of the electromagnets. The applied electrical current may correspond to output steering force(s) necessary to move the endoscope steerable tip by a prescribed amount, along one or more axes.

The electromagnetic steering force generated by one or more electromagnets may be applied to rotational electromagnets of the cartridge (such as rotational electromagnets 752 or rotors 436), which may further transmit the steering forces to mechanical elements of the steerable endoscope associated with control of the endoscope steerable tip. In some examples, the electromagnetic elements of the VL and cartridge may form an axial motor.

In another alternative example, where one or more motors associated with control of the endoscope steerable tip are located in the cartridge or endoscope (such as motors 715B-C), at operation 912, the VL transmits electrical control signals to the motors in response to the received steering inputs. For example, elements of the VL may translate steering inputs into corresponding motor control signals and transmit the control signals to the motors or elements associated with the motors via the electrical interface (such as VL electrical interface 723). The control signals may be received by elements of the cartridge via the corresponding electrical interface of the cartridge (such as cartridge-VL electrical interface 729) and communicated to the motors or associated elements of the motors. In examples where one or more motors are included in the steerable endoscope, motor control signals may be transmitted by the VL to the endoscope, through the detachable cartridge, via electrical interface elements associated with the VL, detachable cartridge, and steerable endoscope.

In operations 908, 910, or 912, force is applied to control the movement of the endoscope steerable tip in accordance with the received steering control inputs of operation 906. The force may be applied during an intubation procedure, while the endoscope is being guided into position in the airway, and/or to augment the view of the camera system of the VL (such as VL camera system 722).

At operation 914, if a breathing tube was pre-loaded over the endoscope, flow proceeds "NO" and, as needed, additional steering inputs may be received for further control of the endoscope steerable tip. For example, a clinician may prefer an alternate view from the endoscope camera system or may choose to reposition the endoscope for another purpose.

At operation 914, if a post-load procedure is being performed, flow proceeds "YES" and the post-load procedure may be carried out by the clinician. At operation 916, in some examples, elements of the VL may detect that the endoscope has been disconnected from the detachable cartridge. In one example, the disconnection may be detected as a removal of the steerable endoscope from the electrical interface. For instance, the steerable endoscope may no longer appear or be detectable on a shared data bus/interface (for instance, on an I2C bus). In another example, sensors of the VL may detect the absence of the steerable endoscope, such as by detecting the absence of magnetic elements associated with the endoscope drums (such as those described in FIGS. 6 and 7A). In yet another example, the cartridge may detect removal of the endoscope, such as by the described methods above, and communicate this condition to the VL over the electrical interface. In examples where the cartridge is disconnected from the VL during post-loading of a breathing tube, the VL may detect disconnection of the detachable cartridge, such as by disconnection of the cartridge from the electrical interface as described above, or by another method.

Following post-loading of the breathing tube, at operation 918, elements of the VL may detect reconnection of the steerable endoscope, which in some examples may include detecting the availability of the steerable endoscope on the electrical interface. For example, when the steerable endoscope is reconnected to the detachable cartridge, the steerable endoscope may receive electrical power and establish communication with the VL via the electrical interface. In other examples, sensors of the VL may detect the presence of magnetic elements associated with the endoscope drums or may detect other elements of the steerable endoscope.

In examples where the cartridge is disconnected from the VL as part of breathing tube post loading, elements of the VL may detect reconnection of the cartridge per the described methods, such as by detecting the presence of the cartridge on the electrical interface. In some examples, the VL may be capable of separately detecting the presence of the cartridge and the presence of the steerable endoscope.

At operation 920, elements of the VL may determine the orientation of the endoscope steerable tip. The removal and handling of the endoscope steerable tip during post-loading of the breathing tube may result in inadvertent or unintended movement of the endoscope steerable tip. While removed from the detachable cartridge, changes to the orientation of the endoscope steerable tip are not detectable by the VL or detachable cartridge, and such changes may affect steering control of the endoscope.

As depicted in FIG. 6 and described above, the VL may include sensors capable of determining the orientation of the endoscope steerable tip by determining the position/orientation of elements of the steerable endoscope. For example, one or more of the endoscope drums may include magnets affixed to, or within, the drum(s), and the VL may include a Hall effect sensor (such as a multi-axis Hall effect sensor) capable of detecting the position of the magnets. The magnet/drum position may correspond the state of the pull wires associated with the endoscope drums, which corresponds to the orientation of the endoscope steerable tip. In other examples, the VL and endoscope may use other methods for determining the position, orientation, and/or state of the endoscope drums, pull wires, or steerable tip.

In some examples, the VL may include sensors which can detect the position/orientation of the endoscope drums when the endoscope proximal end is fully inserted into the detachable cartridge. For example, one or more Hall effect sensors of the VL may be capable of detecting drum magnet position prior to the endoscope being connected/coupled to the detachable cartridge. Accordingly, determining the orientation of the endoscope steerable tip may include receiving sensor data from the from one or more drum sensors (e.g., Hall effect sensors) and determining a drum orientation (e.g., a rotational position) based on the received sensor data. Such drum orientation data may then be used to determine the orientation or position of the steerable tip of the endoscope.

At operation 922, following determination of steerable tip orientation, the VL configures steering control to account for any unintended changes. For example, when the endoscope is initially disconnected from the cartridge the steerable tip may be oriented in a first orientation, such as pointing fully to the "right" (e.g., at a maximum threshold). During post-loading, one or more of the endoscope drums may be unintentionally rotated, which causes the steerable tip to become oriented to a second position, such as pointing fully to the "left". Upon reconnection, the VL may detect that the steerable tip is not in the last known orientation, which was the first orientation, but is now in the second orientation. The VL may reconfigure steering control accordingly, so that dynamic range of steering control correlates with the actual dynamic range of steerable tip movement. For instance, due to the movement to the left, there is now availability to again steer the tip to the right.

In further examples, the VL may provide an indication of the unintended change to steerable tip orientation to the user via the VL display. For instance, the VL may indicate a previous orientation (prior to endoscope disconnection), the new orientation (following reconnection), and/or another alert or notification related to the new steerable tip orientation. In other examples, the VL may provide a feature that automatically re-orients the steerable tip to the previous (first) orientation following reconnection, such as by a user enabling the feature.

Those skilled in the art will recognize that the methods and systems of the present disclosure may be implemented in many manners and as such are not to be limited by the foregoing aspects and examples. For instance, while the above examples are primarily discussed in relation to an endoscope, an introducer may be used, and an endoscope may be considered one example of an introducer in some examples. Further, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Further, as used herein and in the claims, the phrase "at least one of element A, element B, or element C" is intended to convey any of: element A, element B, element C, elements A and B, elements A and C, elements B and C, and elements A, B, and C.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A medical video system comprising:

a video laryngoscope comprising:

a housing having a front surface and a rear surface, wherein the rear surface includes a laryngoscope electrical interface that is substantially flush with the rear surface, a display screen housed within the housing, and a processor;

a cartridge removably attached to the housing of the video laryngoscope, the cartridge comprising a port, an output drive, and first electrical contacts; and at least one retention magnet housed within at least one of the housing or the cartridge;

an endoscope with a proximal end having a drive system and second electrical contacts, the endoscope further having a distal end with a camera, and a pull wire connecting the drive system and the distal end such that movement of the drive system causes articulation of the distal end;

wherein the proximal end of the endoscope is sized to enter the port, align the second electrical contacts with the first electrical contacts, and engage the drive system with the output drive such that movement of the output drive causes movement of the drive system;

wherein the processor is programmed to receive image data from the endoscope camera, display the image data on the display screen of the video laryngoscope, receive a steering input on the display screen, translate the steering input into a movement of the output drive, and transmit a steering signal to cause the movement of the output drive.

2. The system of claim 1, wherein:

the video laryngoscope further comprises:

a motor; and a laryngoscope output drive connected to the motor; and the cartridge further comprises:

a mechanical receiver, connected to the cartridge output drive, that mechanically couples to the laryngoscope output drive when the cartridge is coupled to the video laryngoscope.

3. The system of claim 2, wherein the video laryngoscope is further programmed to:

based on the steering signal, rotate the motor a direction and amount based on the steering input.

4. The system of claim 1, wherein:

the video laryngoscope further comprises:

a stator portion of a motor; and the cartridge further comprises:

a rotor portion of the motor, the rotor portion of the motor mechanically connected to the output drive, wherein, when the cartridge is coupled to the video laryngoscope, the rotor portion of the motor moves due to magnetic flux generated by the stator portion of the motor.

5. The system of claim 4, wherein the video laryngoscope is further programmed to:

based on the steering signal, generate a current through electromagnets of the stator portion to generate the magnetic flux.

6. The system of claim 1, wherein the cartridge further comprises a motor mechanically connected to the output drive, wherein the motor operates based on the steering signal received from the video laryngoscope.

7. The system of claim 6, wherein the video laryngoscope comprises third electrical contacts exposed on the housing, and the video laryngoscope is further programmed to:

transmit the steering signal to the motor via the third electrical contacts.

8. The system of claim 1, wherein the pull wire is a first pull wire and the drive system includes a drum that is connected to the first pull wire and a second pull wire, wherein:

rotation of the drum in a first direction increases tension of the first pull wire and releases tension of the second pull wire; and rotation of the drum in a second direction increases tension of the second pull wire and releases tension of the first pull wire.

9. The medical video system of claim 1, wherein the at least one retention magnet is housed within the housing of the video laryngoscope.

10. The medical video system of claim 9, wherein the display screen is a touch screen and the steering input is received via the display screen.

11. The medical video system of claim 1, wherein the at least one retention magnet is housed within the cartridge.

12. A medical system comprising:

an introducer comprising:

a proximal end including a drum connected to a pull wire; and a distal end that is steerable based on movement of the pull wire; and a cartridge, attachable to a video laryngoscope, the cartridge comprising:

a first electrical interface;

a port that receives the proximal end of the introducer;

an output drive that mechanically connects to the drum in the proximal end of the introducer when the proximal end of the introducer is inserted into the port; and a rotor portion of a motor mechanically connected to the output drive, wherein, when the cartridge is coupled to the video laryngoscope, the rotor portion of the motor moves due to magnetic flux generated by a stator portion of the motor housed within the video laryngoscope.

13. The medical system of claim 12, wherein the cartridge further comprises a motor mechanically connected to the output drive, the motor configured to operate based on steering signals received from the video laryngoscope when the cartridge is coupled to the video laryngoscope.

14. The medical system of claim 12, wherein the cartridge further comprises a mechanical receiver, connected to the output drive, that mechanically couples to a laryngoscope output drive when the cartridge is coupled to the video laryngoscope.

15. The medical system of claim 12, wherein the introducer includes a second electrical interface that couples with the first electrical interface when the proximal end is received in the port.

16. A medical video system comprising:

a video laryngoscope comprising a housing, a display screen, a processor, and first electrical contacts exposed on the housing;

a cartridge removably attached to the housing of the video laryngoscope, the cartridge comprising a port, an output drive, second electrical contacts, and a motor mechanically connected to the output drive, wherein the motor operates based on a steering signal received from the video laryngoscope; and an endoscope with a proximal end having a drive system and third electrical contacts, the endoscope further having a distal end with a camera, and a pull wire connecting the drive system and the distal end such that movement of the drive system causes articulation of the distal end;

wherein the proximal end of the endoscope is sized to enter the port, align the third electrical contacts with the second electrical contacts, and engage the drive system with the output drive such that movement of the output drive causes movement of the drive system;

wherein the processor is programmed to receive image data from the endoscope camera, display the image data on the display screen of the video laryngoscope, receive a steering input, translate the steering input into a movement of the output drive, and transmit a steering signal to the motor via the first electrical contacts.

17. The medical video system of claim 16, wherein the housing of the video laryngoscope houses the display screen, and the housing has a front surface, including the display screen, and a rear surface, wherein the first electrical contacts are positioned on the rear surface of the housing and are substantially flush with the rear surface.

18. The medical video system of claim 17, wherein the rear surface of the housing is a flat, smooth surface, and at least one of the housing or the cartridge further houses at least one retention magnet.

19. The medical video system of claim 16, wherein the pull wire is a first pull wire and the drive system includes a drum that is connected to the first pull wire and a second pull wire, wherein:

rotation of the drum in a first direction increases tension of the first pull wire and releases tension of the second pull wire; and rotation of the drum in a second direction increases tension of the second pull wire and releases tension of the first pull wire.

20. The medical video system of claim 16, wherein the first electrical contacts are formed as one or more conductive pads.

* * * * *